United States Patent

Pye et al.

[11] Patent Number: 5,874,629
[45] Date of Patent: Feb. 23, 1999

[54] CHIRAL BISPHOSPHINES

[75] Inventors: Philip Pye, Guttenberg; Kai Rossen, Westfield; Ralph P. Volante, Cranbury, all of N.J.

[73] Assignee: Merck & Co., Inc., Rahway, N.J.

[21] Appl. No.: 866,665

[22] Filed: Jun. 9, 1997

Related U.S. Application Data

[60] Provisional application No. 60/019,590 Jun. 12, 1996.
[51] Int. Cl.$^6$ .................................................. C07F 9/50
[52] U.S. Cl. ................................................................ 568/17
[58] Field of Search ................................................ 568/17

[56] References Cited

U.S. PATENT DOCUMENTS

| | | | |
|---|---|---|---|
| 5,399,771 | 3/1995 | Cai | 568/17 |
| 5,516,944 | 5/1996 | Broger | 568/13 |

OTHER PUBLICATIONS

H.J. Reich and D.J. Cram, Macro Rings. XXXVII. Multiple Electrophilic Substitution Reactions of [2.2] Paracyclophanes and Interconversions of Polysubstituted Derivatives, J. Am. Chem. Soc., 91(13): 3527–3533 (1969).

S.V. Lindeman et al., Molecular Structure of 4, 16–Dichloro–and 4, 16–Dibromo [2.2]–Paracyclophanes, Izvestiya Akademii Nauk SSSR, Seriya Khimicheskaya, No. 9, pp. 2007–2010 (1986).

*Primary Examiner*—Gary Geist
*Assistant Examiner*—Jean F. Vollano
*Attorney, Agent, or Firm*—Kenneth R. Walton; Melvin Winokur

[57] ABSTRACT

New chiral biphosphines, e.g.,

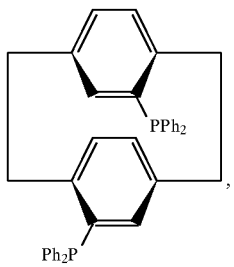

are useful as key components in catalysts for asymmetric reactions, providing desirably high enantiomeric excess (ee).

6 Claims, No Drawings

CHIRAL BISPHOSPHINES

Priority is being claimed under 35 USC 119(e) of the provisional application Ser. No. 60/019,590, filed May 12, 1996.

BACKGROUND OF THE INVENTION

The present application is related to U.S. Ser. No. 60/019,590, now abandoned, the contents of which are hereby incorporated by reference.

Chiral bisphosphines are an important class of chiral ligands that are used to prepare catalysts for the asymmetric homogeneous hydrogenation, transfer hydrogenation, hydrosilylation, hydroboration or hydroformylation of olefines, ketones, imines as well as the enantioselective isomerisation of olefins, the coupling of Grignard reagents and organic halides and the arylation of olefins, e.g., the Heck reaction. A good summary of these reactions is contained in R. Noyori, Asymmetric Catalysis in Organic Synthesis, John Wiley & Sons, 1994 and I. Ojima, Catalytic Asymmetric Catalysis, VCH Publishers, 1994. Known chiral bisphosphines are the following classes: bisphosphines derived from natural products such as DIOP or NORPHOS; bisphosphines with chiral P, such as DIPAMP; substituted 1,2-bis(phospholano)benzene ligands (DuPHOS); and axial chiral compounds of appropriately substituted sterically hindered biphenyls. The most prominent and the synthetically most useful members of the latter class in particular and of known chiral bisphosphines in general are BINAP and TolBINAP, of the structure

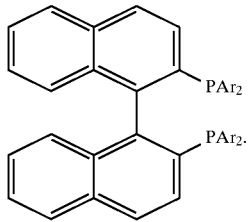

Ar = Ph BINAP
Ar = pCH$_3$—C$_6$H$_4$ TolBINAP

Asymmetric catalysts based on BINAP often provide high enantiomeric excess (ee) in a variety of reaction types. Unfortunately, a number of substrates or reactions result in undesirably low ee, so that more cumbersome classical resolution procedures have to be applied.

In the present invention a novel set of bisphosphine ligands is described, which are appropriately substituted cyclophanes with planar chirality. The present invention covers enantiomers of pseudo-ortho substituted cyclophanes. In one example, the bisphosphines of the present invention form complexes used to synthesize a chiral intermediate for the AIDS drug CRIXIVAN® (trademark of Merck & Co., Inc.).

The chiral biphosphines of the present invention provide desirably high enantiomeric excess as catalysts in a variety of asymmetric reactions.

BRIEF DESCRIPTION OF THE INVENTION

The present invention provides new chiral biphosphines suitably used as catalysts in asymmetric reactions.

TABLE OF ABBREVIATIONS

| | |
|---|---|
| BINAP | 2,2'-bis(diphenylphosphino)-1,1'-binapthyl |
| Boc | t-Butyl oxycarbonyl |
| Boc-BPPM | (2S,4S)-tert-Butyl 4-(diphenylphosphino)-2-(diphenyl-phosphinomethyl)-2-pyrrolidine-carboxylate |
| C$^\ominus$ | counterion |
| Cbz | Benzyl oxycarbonyl |
| COD | 1,5-cyclooctadiene |
| DIOP | (R,R)-2,3-O-isopropylidene-2,3-dihydroxy-1,4-bis-(diphenylphosphino)-butane |
| DIPAMP | (RR)-1,2-bis((o-methoxyphenyl)phenylphosphino)ethane |
| DUPHOS | 1,2-Bis((2S,5S)-2,5-diethylphospholano)benzene |
| NORPHOS | [(2R,3R)-8,9,10-trinorborn-5-ene-2,3-diyl]-bis(diphenylphosphine) |
| PROPHOS | 1,2-bis(diphenylphosphino)propane |
| SKEWPHOS | 2,4-bis(diphenylphosphino)pentane |
| TfO | triflate |

DETAILED DESCRIPTION OF THE INVENTION

Pseudo-ortho-substituted chiral bisphosphines of the present invention are useful for preparing complexes that act as catalysts in a variety of asymmetric reactions, including asymmetric homogeneous hydrogenation, transfer hydrogenation, hydrosilylation, hydroboration or hydroformylation of olefines, ketones, imines as well as the enantioselective isomerisation of olefins, the coupling of Grignard reagents and organic halides and the arylation of olefins. Methods for the preparation and use of the chiral bisphosphines and their complexes are also described.

The present invention encompasses compounds of the formulae

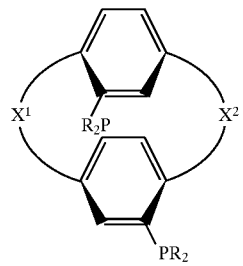

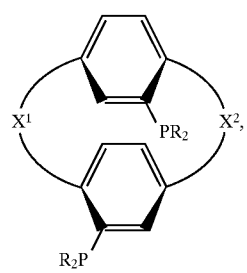

wherein R is C$_{1-4}$ alkyl, C$_{3-6}$ cycloalkyl, or aryl unsubstituted or substituted with —F, —CH$_3$, —CF$_3$ or CH$_3$O—; and X$^1$ and X$^2$ link the two R$_2$P-substituted benzenes and independently form a 2 to 4 membered link consisting of 2 to 4 carbon atoms and up to one unsubstituted or substituted heteroatom selected from O, S, SO,

One embodiment of the present invention is limited to compounds wherein the number of atoms in the $X^1$ link is the same as the number of atoms in the $X^2$ link.

One preferred embodiment is the compound 4,12-bis[diphenylphosphino]-2,2-paracyclophane known herein as PLANEPHOS.

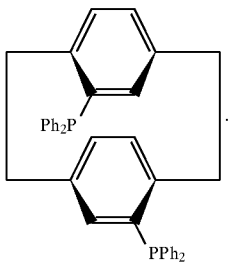

The present invention also encompasses a complex for catalysis of a variety of asymmetric reactions. The complex of the present invention is (BISPHOS) M→$L_n$, wherein n is an integer and is 0, 1, 2, 3 or 4;
M is Rh, Ir, Ru or Pd;
L is a ligand reversibly coordinated for replacement by substrate;
BISPHOS is a compound of the formulae

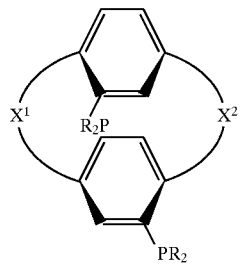

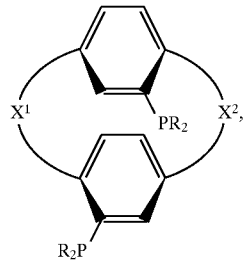

wherein R is $C_{1-4}$ alkyl, $C_{3-6}$ cycloalkyl, or aryl unsubstituted or substituted with —F, —$CH_3$, —$CF_3$ or $CH_3O$—; and
$X^1$ and $X^2$ link the two $R_2P$-substituted benzenes and independently form a 2 to 4 membered link consisting of 2 to 4 carbon atoms and up to one unsubstituted or substituted heteroatom selected from O, S, SO, $SO_2$, or

One embodiment of the present invention is limited to a complex, wherein the ligand is (a) norbornadiene;

(b) $C_{1-4}$ OH;

(c) $NR^1R^2R^3$, and $R^1$ and $R^2$ and $R^3$ are independently H, $C_{1-4}$ alkyl, $C_{3-7}$ cycloalkyl, aryl, pyridyl, or tetrahydrofuryl; or (d) a diene of the formula

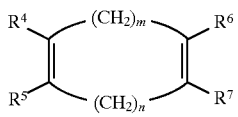

wherein m is an integer and is 1, 2, 3 or 4; n is an integer and is 0,1,2,3 or 4; and $R^4$, $R^5$, $R^6$ and $R^7$ are independently H, $C_{1-4}$ alkyl;

(e) ether, of the formula $R^1OR^2$, or a cyclic ether of the formula

wherein p is an integer and is 2, 3, 4 or 5;

(f) bis-ether, of the formula

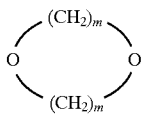

wherein m is defined as above;

(g) bis-alcohol of the formula

HO—$(CR^8R^9)_p$—OH wherein p is defined as above; and
$R^8$ and $R^9$ are independently H, $C_{1-4}$ alkyl or aryl; or (h) ethylene.

Another embodiment of the present invention is limited to a complex, wherein the number of atoms in the $X^1$ link of BISPHOS is the same as the number of atoms in the $X^2$ link of BISPHOS.

Another embodiment of the present invention is limited to a complex, wherein M is Rh or Ir, n is 1 and L is cyclooctadiene.

Another embodiment of the present invention is limited to a complex of the structure

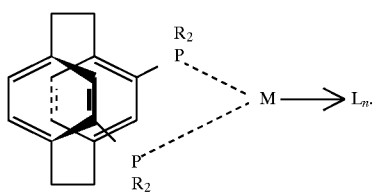

Another embodiment of the present invention is limited to a complex of the structure

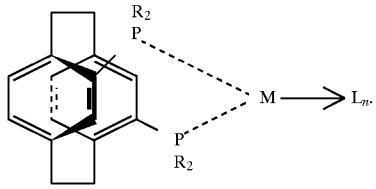

Another embodiment of the present invention is limited to the complex

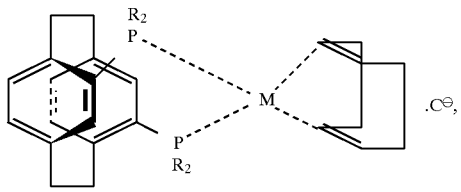

wherein M is Rh or Ir.
Another embodiment of the present invention is limited to the complex

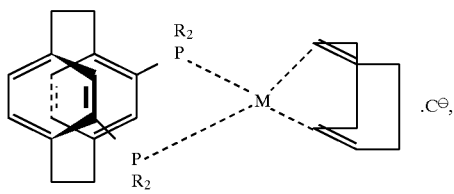

wherein M is Rh or Ir.
Another embodiment of the present invention is limited to the complex

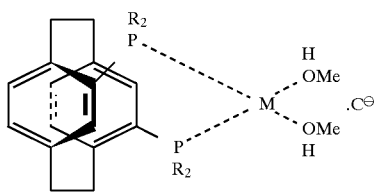

or

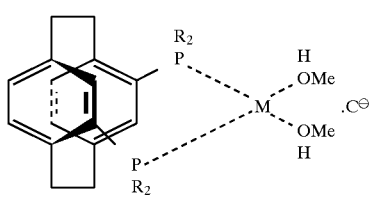

wherein M is Rh or Ir.

Another embodiment of the present invention is limited to the complex

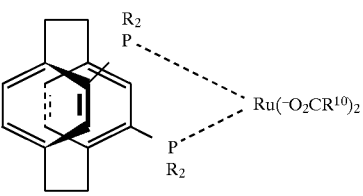

or

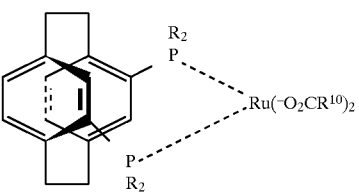

wherein $R^{10}$ is $CF_3$ or $CH_3$.

Another embodiment of the present invention is limited to the complex

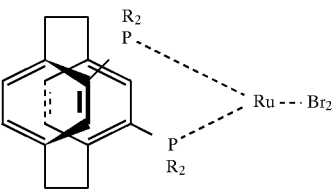

or

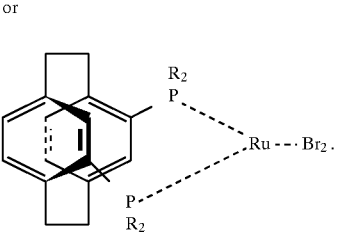

Another aspect of the present invention is a partly or completely enantiomerically pure compound of the formula

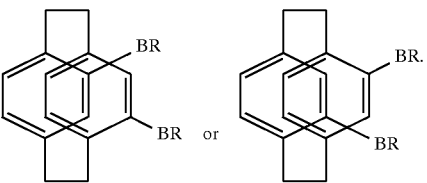

Preferably, a completely enantiomerically pure compound of the formula

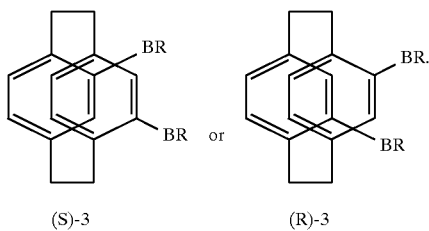

(S)-3         (R)-3

Still another embodiment of the present invention is a process for forming a chiral bisphosphine compound (S)-40

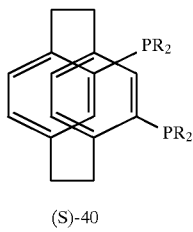

(S)-40 wherein R is $C_{1-4}$ alkyl, $C_{3-6}$ cycloalkyl, or aryl unsubstituted or substituted with —F, —$CH_3$, —$CF_3$ or $CH_3O$—; comprising the steps of (a) treating a racemic phosphinyl compound 41

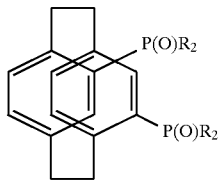

rac-41 with a resolving agent to afford chiral (S)-41; and
(b) reducing the chiral (S)-41 to provide the chiral bisphosphine compound (S)-40

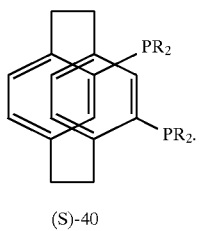

(S)-40

Additionally, it is apparent to one of ordinary skill in the art that this process can also be used to form the (R)-chiral enantiomer

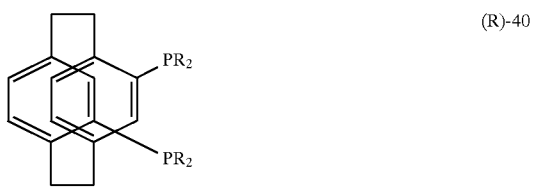

(R)-40

Preferably, the resolving agent used in this process is dibenzoyl-L-tartaric acid and each R is phenyl.

In the complexes of the present invention a wide variety of ligands are suitable. Any ligand that reversibly coordinates and can be replaced by the substrate is appropriate, including the solvent for the reaction. Suitable ligands include, but are not limited to, dienes, such as cyclooctadiene or norbornadiene, lower alcohols, ethers, cyclic ethers, bis-ethers, bis-alcohols, and simple olefins, such as ethylene. One preferred ligand is cyclooctadiene. The metal M is selected from Rh, Ir, Ru, or Pd.

The complexes formed according to the present invention comprise a chiral bisphosphine, a metal (M) selected from Rh, Ir, Ru or Pd, one or more ligands, and, optionally, a counterion($C^\ominus$). Suitable counterions are non-nucleophiles and include, but are not limited to, $OTf^\ominus$, $ClO_4^\ominus$, $SbF_6^\ominus$ or $PF_6^\ominus$. It is understood that any formula for a complex in the present invention includes, if appropriate, a counterion.

To illustrate the use of the chiral bisphosophines and their complexes, applicants demonstrate the synthesis of the chiral intermediate

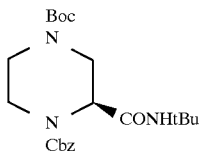

for the synthesis of the known efficacious HIV protease inhibitor CRIXIVAN®, compound J in the Examples below.

The pseudo-ortho substituted bisphosphines of the present invention are catalysts in a variety of known reactions, including but not limited to 1. chiral hydrogenation of enamide structures, e.g.,

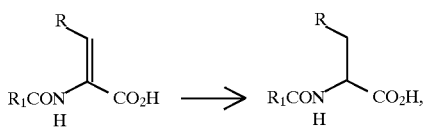

2. chiral hydrogenation of non-enamide structures, e.g.,

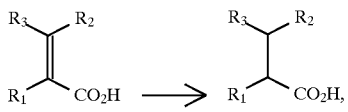

3. asymmetric hydrogenation in isoquinoline synthesis, e.g.,

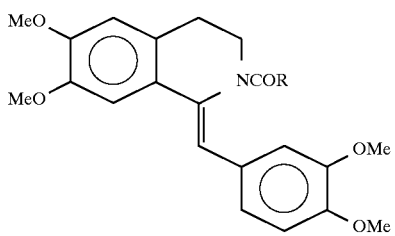

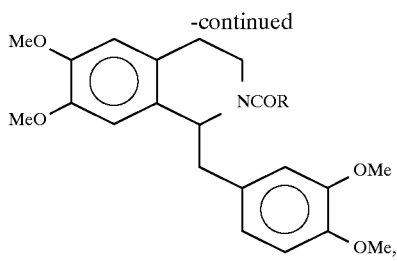

4. asymmetric hydrogenation in unsaturated alcohols, e.g.,

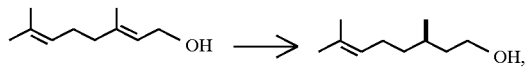

5. asymmetric hydrogenation in non-chelating substitution, e.g,

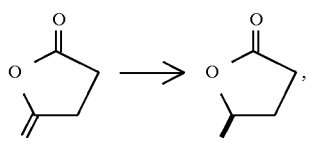

6. hydrogenation of ketones, e.g.,

7. double hydrogenation of 1,3 and 1,2 ketones, e.g.,

8. enantioselective isomerization of olefins, e.g.,

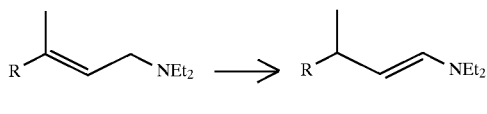

9. asymmetric hydrogenation of imines, e.g.,

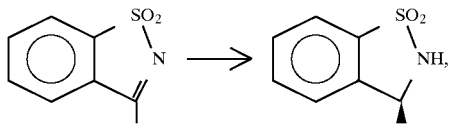

10. asymmetric—hydroboration, e.g.,

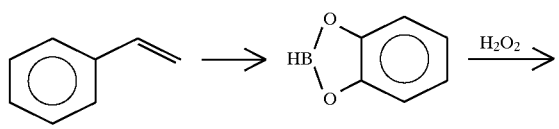

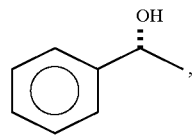

11. asymmetric cyclization of olefinic aldehydes, e.g.,

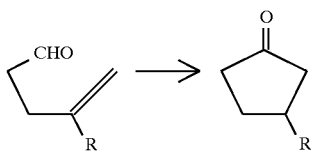

12. arylation of olefins, e.g.,

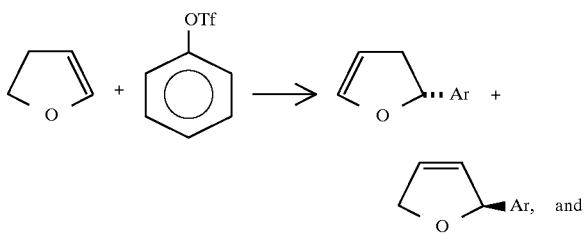

13. asymmetric alkylation, e.g.,

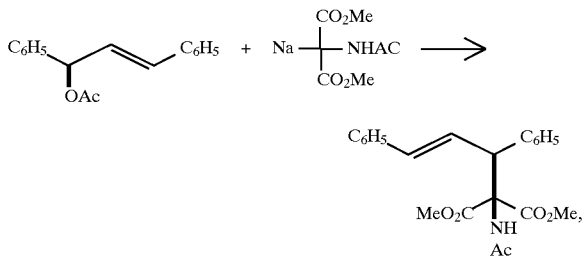

14. amination of aryl-halides (Hartwig-Buchwald reaction)

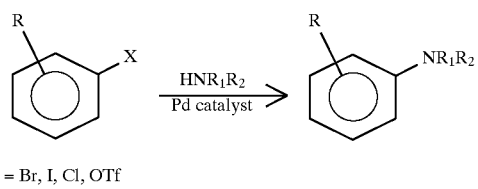

X = Br, I, Cl, OTf

PREPARATION

While the bisphosphine based on the [2.2]paracyclophane system gives excellent asymmetric catalysts, some substrates require differently engineered metal/ligand combinations in order to achieve high chemical conversions in high ee. A striking feature of the [2.2] paracyclophane system is the rigidity enforced by the close proximity of the 2 benzene rings and it is possible to introduce some flexibility into these systems by enlarging the ring size from the [2.2] to the [2.3], [3.3], [3.4], [4.4] and [2.4] systems. While the enlarged ring size in these systems allows for some conformational flexibility, the substituted benzene rings are still not able to rotate, so that the resolved materials are configurationally stable. Additionally, introduction of heteroatoms into the bridge can lead to desirable effects, such as increased solubility and different polarity. In the following the synthetic access to these ring enlarged cyclophanes is described.

BISPHOSPHINES WITH PLANAR CHIRALITY

A new class of C-2 symmetric bis-phosphine ligands of general structure I is described in this invention. It is a paracyclophane with carbon and/or heteroatom bridges. The [2.2], [2.3], [3.3], [3.4], [2.4] and [4.4] paracyclophanes are all configurationally stable.

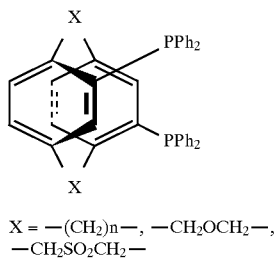

$X = -(CH_2)n-, -CH_2OCH_2-,$
$-CH_2SO_2CH_2-$

The easiest access to these systems is through the commercially available [2.2] paracyclophane II which is brominated to afford four isomeric dibromides [see Reich and Cram; J. Am. Chem. Soc. 1969, 91, 3527.] (Scheme 1). The pseudo-para isomer 4 is crystallized from hexanes whereas the desired pseudo-ortho isomer IV is obtained through a chromatography of the mother liquors.

SCHEME I

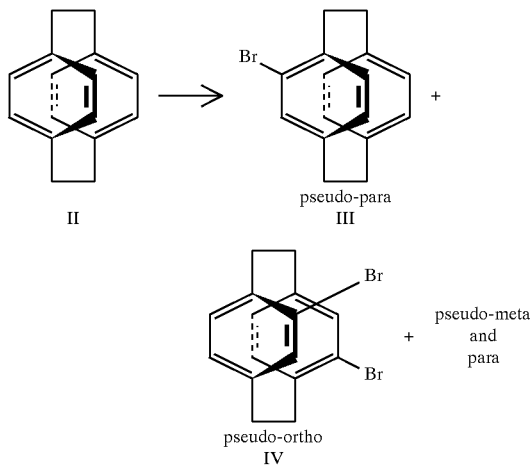

Incorporation of the diphenyl phosphino groups is achieved in one of three ways: Scheme 2 shows the direct displacement of Br by the diphenylphosphino group. Although these routes are highly efficient, the ease of oxidation of V under the reaction conditions makes this approach less attractive.

SCHEME 2

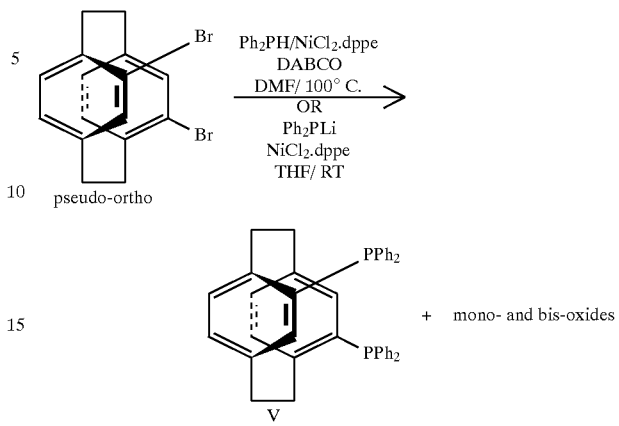

Scheme 5 (below) shows the preferred route.

In Scheme 5, following a low temperature lithiation with BuLi, transmetallation with $MgBr_2$ leads to the Grignard reagent.

Alternatively, the Grignard reagent can be prepared directly from Mg and pure pseudo-ortho-dibromide IV.

The Grignard reagent is subsequently reacted with diphenyl phosphoryl chloride to give the biphosphine oxide IX.

Alternatively, the trans-metallation to the Grignard can be avoided by using the bislithio compound directly, eventually with the addition of additives, for example, tetramethyl ethylene diamine.

In the last step, the phosphine oxide can be reduced to the phosphine using standard conditions, e.g., with $HSiCl_3$ or $LiAlH_4$. The optical resolution can be performed in one of three ways: In the simplest resolution, chromatography of the pseudo-ortho-dibromide IV on a chiral stationary phase affords the optically pure pseudo-ortho-dibromide. For e.g., the enantiomers of IV are readily separated on crystalline cellulose triacetate using EtOH as eluent. Equally good separation are obtained using the commercial Chiracell and Chiralpak columns. Subsequent direct introduction of the diphenylphosphino group or the two step introduction by first introducing the diphenylphosphine oxide group followed by reduction thus gives the optically pure biphosphine ligand V.

Alternatively, racemic biphosphine oxide IX is prepared. This material can be resolved by the formation of inclusion complexes with chiral substances, e.g., benzoyltartanrc acid or N-benzylchinchonidinium salts. The resolved phosphine oxide is separated from the resolving agent and obtained in optically pure form. Reduction of the phosphine oxide is accomplished in a variety of ways, e.g., $HSiCl_3$ with $Et_3N$ or preferably $HSiCl_3$ alone.

Thirdly, optically pure pseudo-ortho-dibromide can be obtained from racemic material using a kinetic resolution. Thus, reaction of the racemic material with a primary amine and sodium-tert-butoxide catalyzed by a chiral Pd-biphosphine complex leads to the preferential reaction of one of the enantiomers, leaving optically pure IV behind. An especially attractive Pd catalyst is obtained with the chiral ligand V. With this ligand one of the enantiomers of IV reacts 3–5 times as fast as the other, leaving optically pure IV behind. Addition of a thallium salt increases this chiral discrimination to a very practical 10–15 fold rate difference.

In order to test the efficacy of the bis-phosphine ligand in a rhodium catalyzed hydrogenation reaction, the complex VI is synthesized. Scheme 3.

SCHEME 3

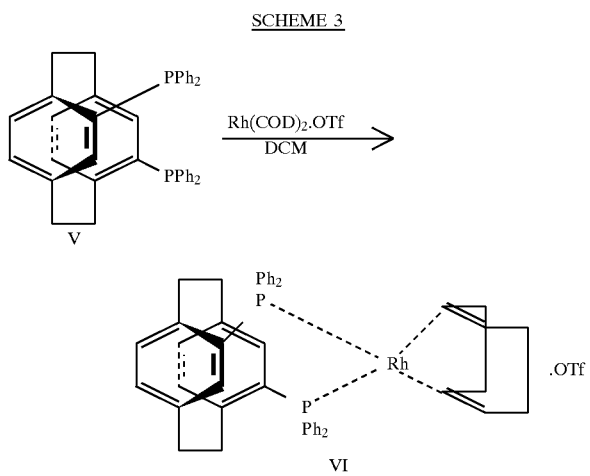

When VI is added to a methanolic solution of α-acylaminocinnamic acid VII and hydrogen applied at 1000 psi, the phenyl alanine derivative VIII is obtained (Scheme 4).

SCHEME 4

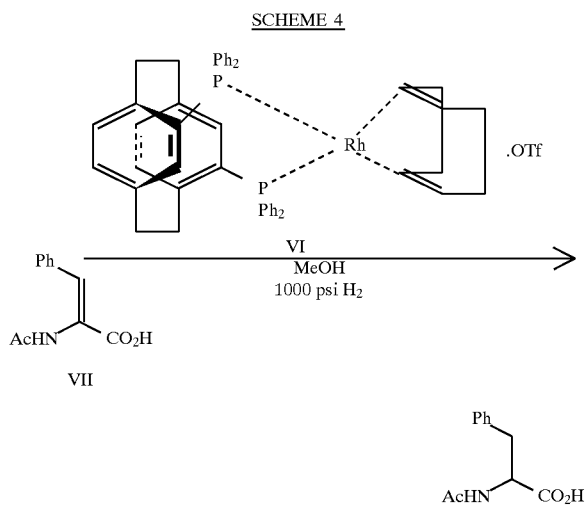

Hydrogenation of the pre-catalyst VI in methanol leads to the loss of the cyclooctadiene ligand to yield VIa

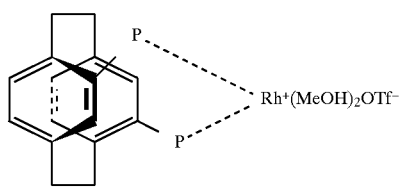

The formation of catalyst VIa prior to substrate addition makes it possible to perform hydrogenations at reduced temperatures as low as about −45° C. (Scheme 4a).

SCHEME 4a

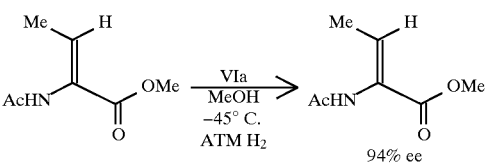

Due to the lability of V the resolution was attempted through the more robust bis-phosphine oxide IX. Treatment of the bis-Grignard reagent with Ph$_2$POCl afforded IX (Scheme 5).

Scheme 5 shows the preferred route:

SCHEME 5

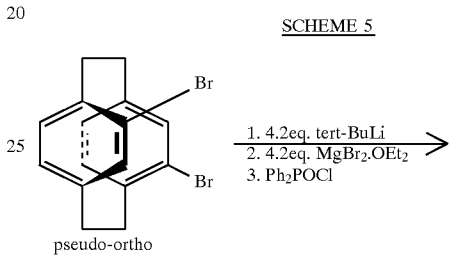

The mixture rac IX is resolved using inclusion complexes with chiral substances, e.g., benzoyltartaric acid or N-benzylchinchonidinium salts. The resolved phosphine oxide is separated from the resolving agent and obtained in optically pure form. Reduction of the phosphine oxide is accomplished in a variety of ways, e.g., HSiCl$_3$ with Et$_3$N or preferably HSiCl$_3$ alone.

Bromination of the bridge under radical conditions leads to the compounds XI and XII.

SCHEME 6

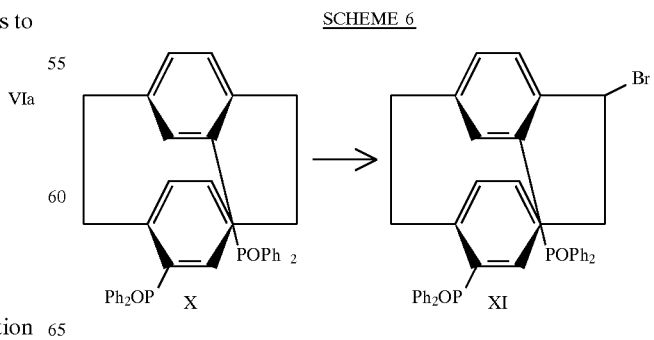

+

-continued
SCHEME 6

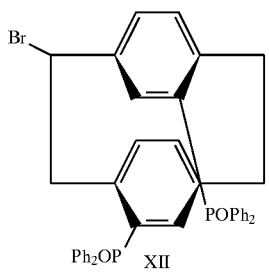

Simply changing the stoichiometry in the bromination and using 2 equivalents of Br$_2$ leads to a mixture of the bisbrominated products XIII and XIV, which are again difficult to separate (Scheme 7).

SCHEME 7

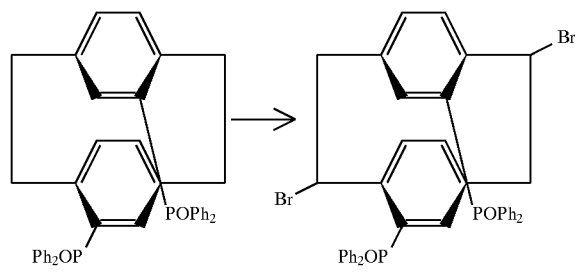

Simple hydrolysis of the bromides with either NaOAc/HOAc followed by base or use of a silver salt leads cleanly to the corresponding alcohols, that can be readily seperated on silica gel (Scheme 8).

SCHEME 8

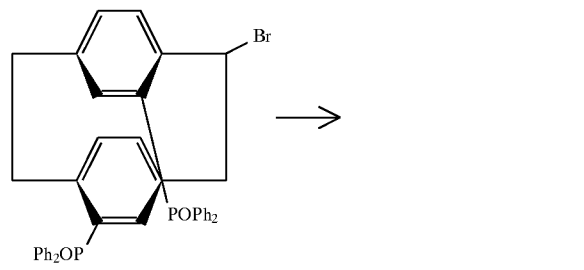

-continued
SCHEME 8

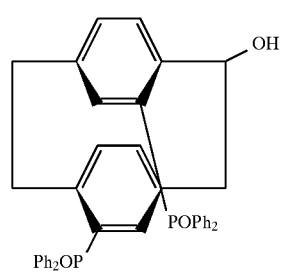

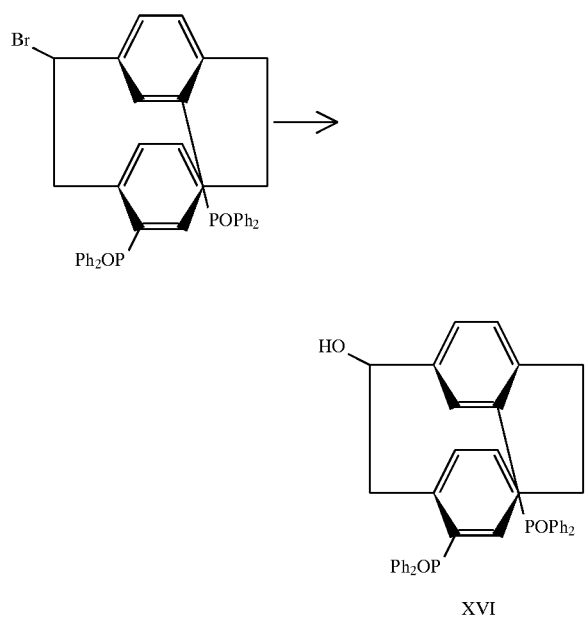

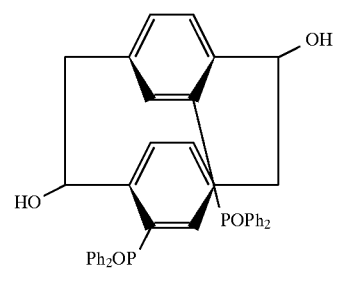

SCHEME 8 -continued

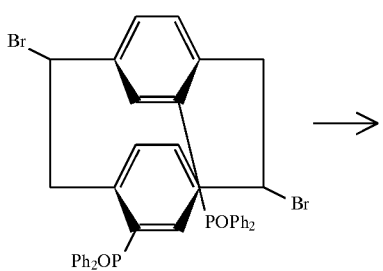

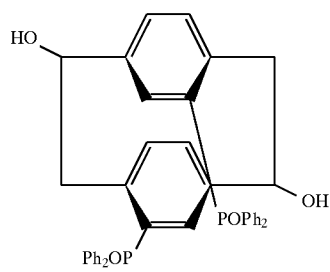

XVIII

The subsequent reactions are performed on the enantiomerically pure diastereomers XV to XVIII and they consist of the following sequence of classical reactions. They are shown as an example only for compound XIX in Scheme 9, but this sequence of reactions holds for all such alcohol derivatives.

SCHEME 9

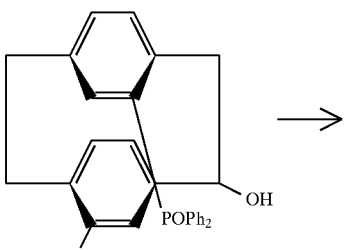

XIX

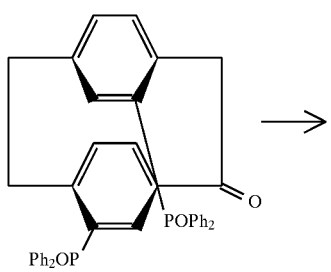

SCHEME 9 -continued

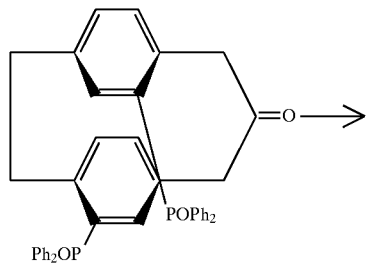

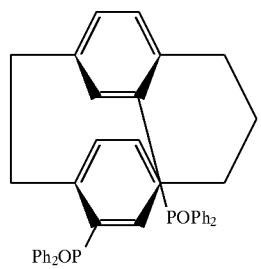

Initially the alcohol is oxidized to the corresponding ketone using Swern conditions or a variety of metal based oxidants, such as pyridinium dichromate or tetrapropylammonium perruthenate. The ketone is then subjected to a ring expansion using either diazomethane or trimethylsilyldiazomethane or Demjanow conditions after first adding either nitromethane or cyanide to the ketone and reducing it down to the aminomethyl group. The resulting ring-expanded ketone is subsequently reduced to the corresponding methylene group. This is best accomplished using the Huang-Minlon modification of the classical Wolff-Kishner reduction (DMSO, potassium-tert-butoxide, hydrazine) or the Clemmenson reduction conditions (Zn, dilute HCl). The resulting [2.3]paracyclophane is chiral, but not C2 symmetric. Reduction of the two ketones derived from the bisbromides of Scheme 3 gives the same C2 symmetric [3.3] system for both starting materials so that for practical reasons the mixture of the bis-bromides can be carried through this ring expansion sequence without separating any of the diastereomeric mixtures that are formed during the reaction sequence. As before, the phosphine oxides are cleanly reduced to the phosphine with $SiHCl_3/Et_3N$ and the resulting bisphosphines are listed in Scheme 10.

SCHEME 10

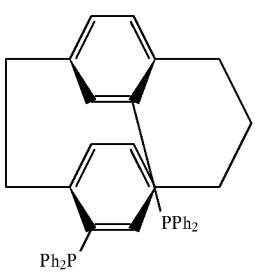

-continued
SCHEME 10

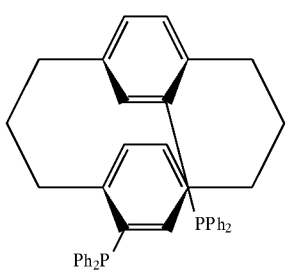

The enantiomers of Scheme 5 are then used to prepare the active Rh, Ir, Ru or Pd catalysts as described for the [2.2]paracyclophane bisphosphine in Example 6, or using procedures similiar to those described in the literature for known bisphosphines.

In summary, a sequence of classical reactions allows for the preparation of the [2.3] and the [3.3]paracyclophan bisphosphines from the readily available enantiomerically pure [2.2]paracyclophan bisphosphineoxide. It is readily apparent to a skilled artisan that the same synthetic strategy consisting of a radical bromination of the bridge, followed by hydrolysis of the bromide to the alcohol, oxidation of the alcohol to the ketone, ring expansion and reduction of the ketone to the methylene group furnishes [2.4] paracyclophane when [2.3]paracyclophane is used as starting material and the [3.4]paracyclophanes when the [3.3] paracyclophane is the starting material for the ring expansion sequence. A further analogous ring expansion is possible to prepare the [4.4] system, but further ring expansion leads to systems that are configurationally stable only at low temperatures and are therefore of limited practical use (Scheme 11).

SCHEME 11

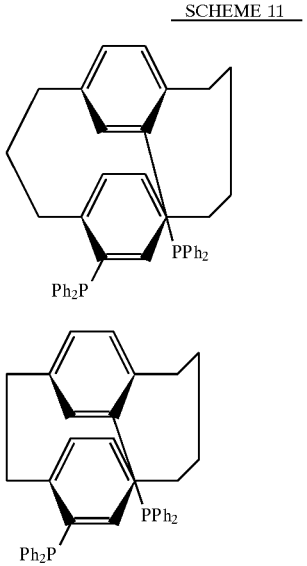

-continued
SCHEME 11

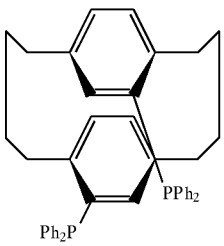

Useful background information on simple unsubstituted systems is found in *J. Am. Chem. Soc.* 88, 3513(1966) and *J. Am. Chem. Soc.* 88, 3667 (1966). The application of these methods to the resolved, enantiomerically pure phosphinoxides is novel and leads to a family of chiral bisphosphines that are useful for the preparation of catalysts for asymmetric catalytic reactions.

NON-C2 SYMMETRIC CHIRAL BISPHOSPHINES: ALTERNATIVE SYNTHESIS

An alternative, operationally simple preparation of the chiral, but no longer C2 symmetric [2.4]paracyclophane bisphosphine also commences with the [2.2]paracyclophane bisphosphineoxide XXX. A ring expansion of the unsubstituted [2.2]paracyclophane to the [2.4]paracyclophane is described in *J. Am. Chem. Soc.* 89, 3078(1967). Thus, heating of X to approximately 200° C. in dimethyl flmarate or dimethyl maleate leads to the clean formation of the ring expanded system as a mixture of XX and XXI. As enantiomerically pure X racemises during this ring expansion, the synthesis uses the racemic X and a resolution is required for XX or XXI (Scheme 12).

SCHEME 12

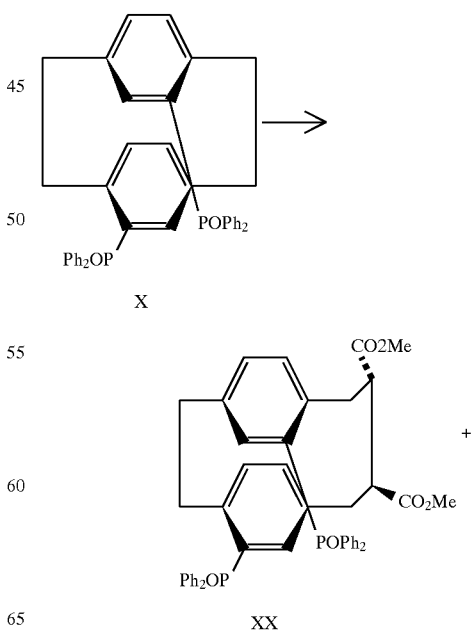

-continued
SCHEME 12

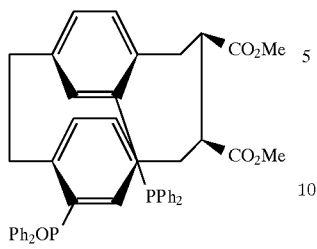

XXI

Scheme 12 is easily accomplished by hydrolizing the ester to the acid and the acids are then resolved in a classical fashion with a chiral amine. For this purpose phenethylamine and brucine are suitable.

Alternatively, it is possible to resolve the enantiomers on a chiral chromatography column. After the resolution, various chemical transformations of the vicinal carboxymethoxy groups lead to chiral, but not C2 symmetric, bisphoshine catalyst precursors. For example, treatment of the acid with lead tetraacetate and lithium chloride gives the bis-chloride XXII, and dehalogenation then leads to the unsubstituted methylene bridge. See e.g., *J. Am. Chem. Soc.* 89, 3078, (1967) and Scheme 13:

SCHEME 13

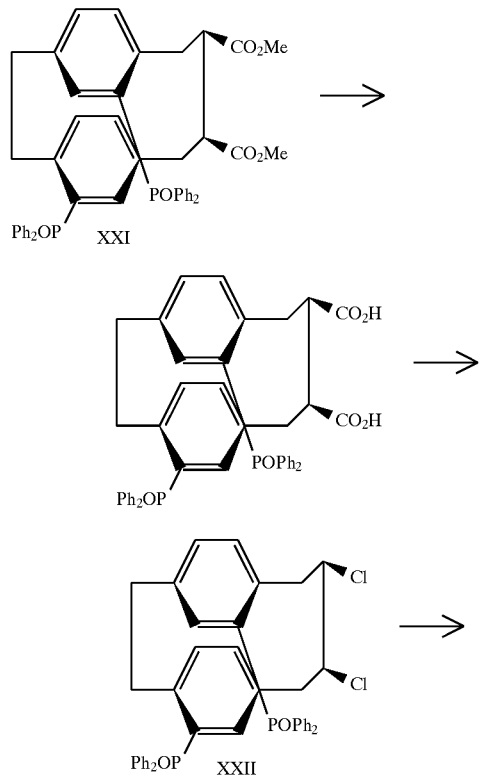

-continued
SCHEME 13

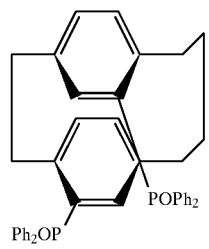

The use of lead tetraacetate in the presence of oxygen leads to the olefin XXIII. See, e.g., *Org. React.* 1972, 19, 279 and Scheme 14:

SCHEME 14

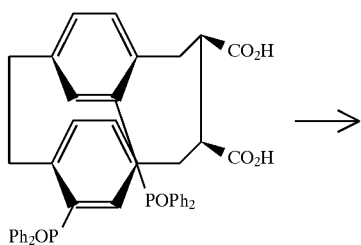

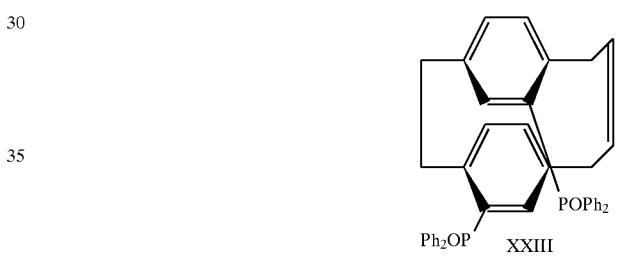

XXIII

Subsequent reduction of the phosphinoxides to the phosphin with SiHCl$_3$/Et$_3$N leads to the generation of the chiral phosphines, that are used to prepare the Rh, Ru, Ir and Pd catalysts.

HETEROATOM-SUBSTITUTED CHIRAL BISPHOSPHINES

In addition to the pure C bridges in the bisphosphin paracyclophanes described above, the incorporation of heteroatoms in the bridge leads to improved solubilities, polarity and a slight change in the preferred conformation of the system. Thus, the C2 symmetric bis-oxa [3.3] paracyclophane bisphoshine XXV is prepared by brominating the known unsubstitued bis-oxa [3.3] paracyclophane with Lewis acid catalyst (FeBr$_3$) and Br$_2$ and the resulting mixture of ring brominated compounds is separated by chromatography on SiO$_2$ and Al$_2$O$_3$. The chromatography gives a clean fraction of the pseudo ortho dibromide XXIV, which is transformed into the bisphosphinoxide as described above for the [2.2]paracyclophane (t-BuLi, MgBr$_2$; Ph$_2$POCl). Resolution of the resulting racemate is accomplished by forming the inclusion complex with di-benzoyltartrate or by chromatography on a chiral medium. Subsequently, the resolved phosphineoxides are reduced using the standard conditions (HSiCl$_3$, Et$_3$N) and the resulting optically pure bisphosphines XXV are then used to prepare the asymmetric catalysts with Rh, Ru, Ir, and Pd (Scheme 15).

SCHEME 15

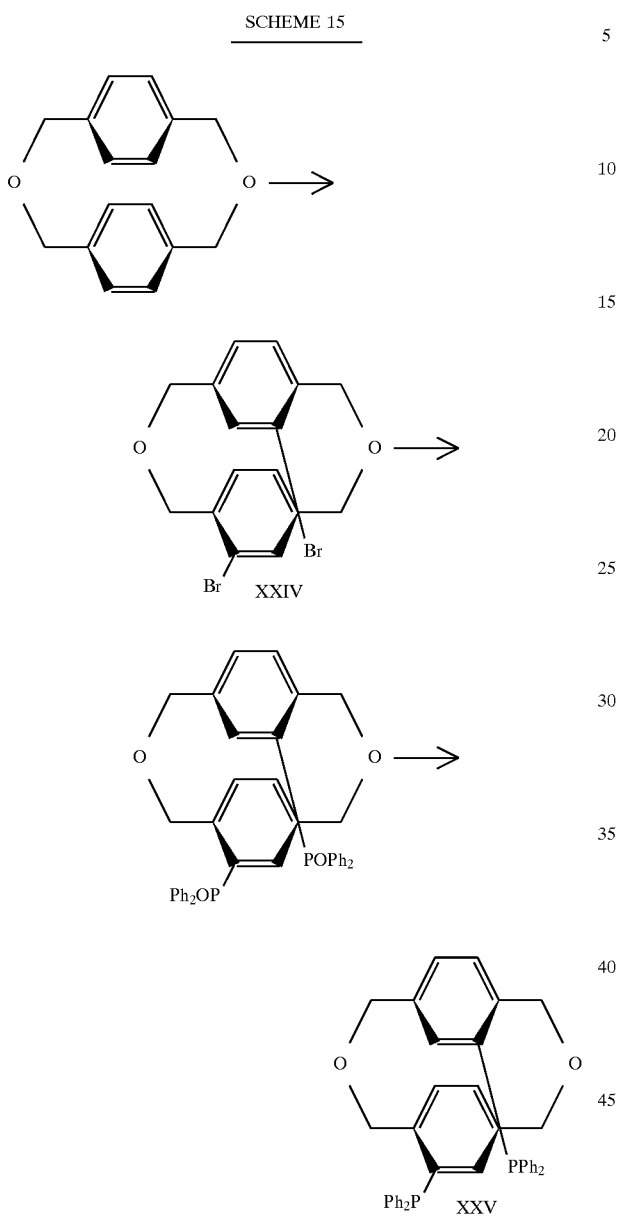

SCHEME 16

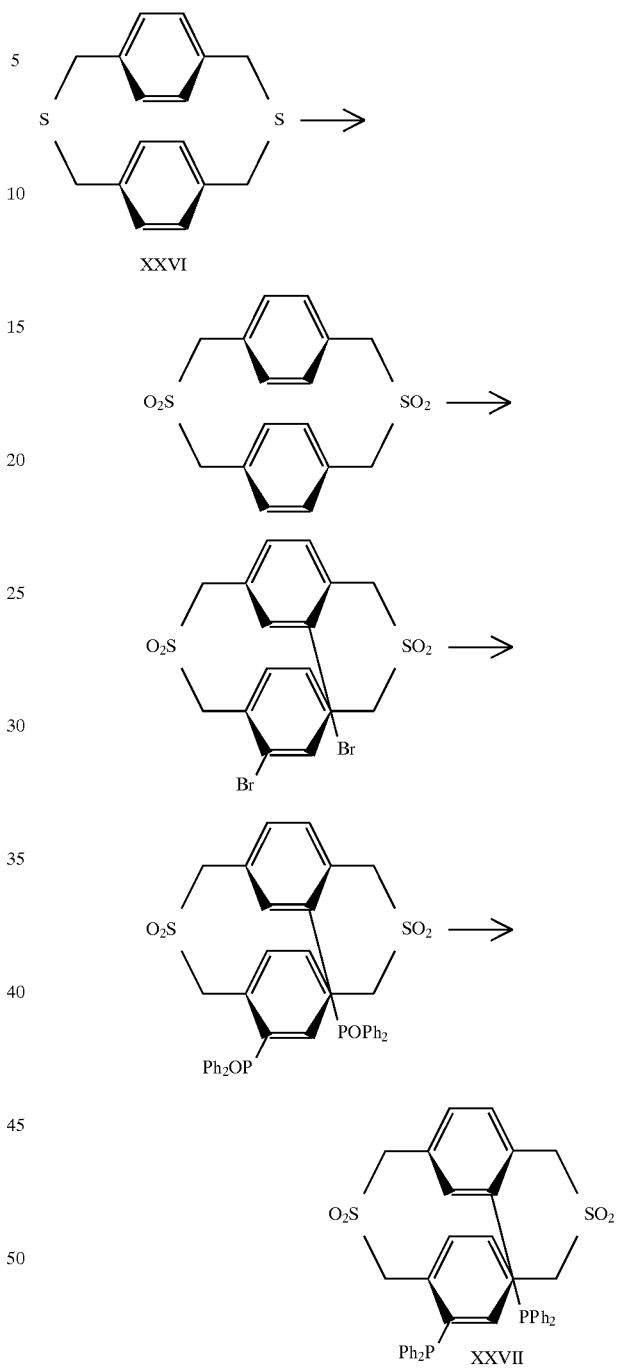

Oxidation of the known bis-thia [3.3]paracyclophane XXVI with $H_2O_2/Na_2WO_4$ leads to the corresponding sulfone. Subsequent application of the synthetic sequence described above, including Lewis acid catalysed ring bromination, formation of the bis-lithium compound and transmetalation to the Grignard, reaction with $Ph_2POCl$, resolution into the enantiomers and reduction of the phosphineoxides to the phosphines, leads to enantiomerically pure XVII. See Scheme 16. These can be used to prepare catalysts for asymmetric transformation with Rh, Ru, Ir and Pd.

When any variable (e.g., aryl, $X^1$, $X^2$, R, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl).

As used herein, with exceptions as noted, "aryl" is intended to mean phenyl (Ph) or naphthyl.

The compounds of the present invention, may have asymmetric centers and occur as racemates, racemic mixtures and as individual diastereomers, or enantiomers with all isomeric forms being included in the present invention. Unless specifically provided otherwise, a given enantiomer also implies its enantiomer or pair. Also, combinations of solvents, substituents and/or variables are permissible only if such combinations result in stable compounds.

Representative experimental procedures utilizing the novel process are detailed below. These procedures are exemplary only and are not limitations on the novel process of this invention.

EXAMPLE 1

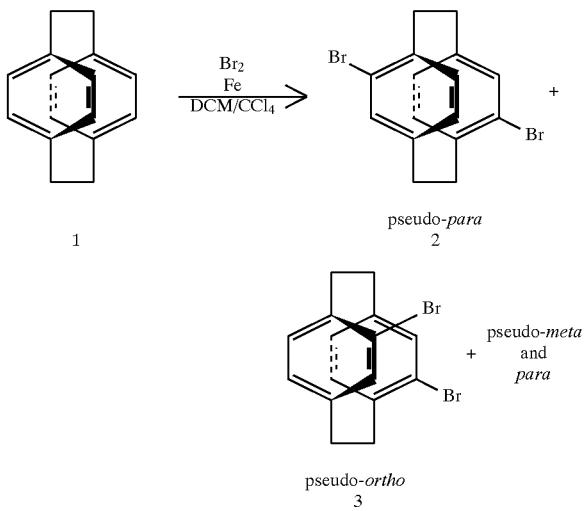

ref: Reich, H. J. and Cram, D. J. *J. Am. Chem. Soc* 1969, 91 (13), 3527.

| | |
|---|---|
| [2.2]paracyclophane | 37.6 g (0.180 mol) |
| Bromine | 58.3 g (0.364 mol) |
| Methylene Chloride | 1100 mL |
| Iron powder | 0.60 g |

Bromine (15.5 g) was added to a stirred suspension of iron powder in methylene chloride (300 mL). After one hour [2.2]paracyclophane (37.6 g) and methylene chloride (800 mL) were added and the reaction was heated to reflux. The remainder of the bromine (42.8 g) was added dropwise over 3 hours and heating continued for a further 4 hours. The reaction mixture was washed with 10% aqueous sodium bisulfite (2×150 mL), brine (1×150 mL) and dried (MgSO$_4$). Evaporation of the solvent afforded an off white solid (55.0 g; 83%, mixture of four dibromides). The solid was dissolved in hot chloroform (500 mL) and diethyl ether (300 mL) was added. The solids were filtered to afford pseudo-para- dibromide 2. After cooling to 0° C. a second crop of pseudo-para- dibromide 2 was obtained and combined with the above (combined yield 15.2 g, 23%). The mother liquors were concentrated, heated in hexanes and filtered. The hexane mother liquors were concentrated and subjected to chromatography on silica gel. Pseudo-ortho-dibromide 3 was obtained as a white solid (8.3 g, 70% pure by LC). NMR data for 2 and 3 in agreement with literature.

EXAMPLE 2

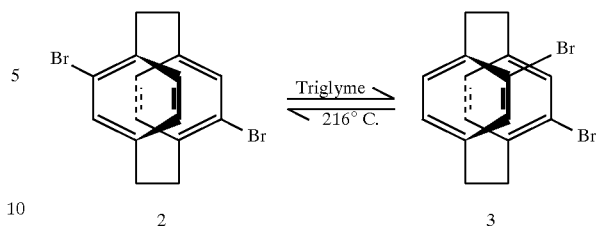

| | |
|---|---|
| Pseudo-*para*-dibromo-[2.2]paracyclophane 2 | 10.5 g (0.029 mol) |
| Triethylene glycol dimethyl ether | 40 mL |

A slurry of 2 in 40 mL of triethylene glycol dimethyl ether was heated at 210° C. for 18 hours. Upon cooling the solids were filtered and resubjected to the above conditions. Upon cooling the solids were filtered again to yield pseudo-para-dibromide 2 (900 mg). The mother liquors from both reactions were combined and the solvent removed by distillation. Filtration through a silica gel plug afforded pseudo-ortho-dibromide 3 as a white solid (6.70 g, 64%).

EXAMPLE 3

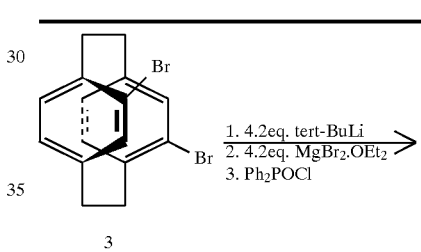

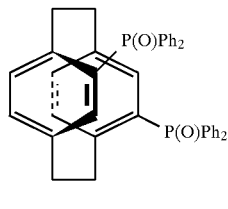

| | |
|---|---|
| Pseudo-ortho-dibromo-[2.2]paracyclophane 3 (~70% pure) | 4.80 g (9.2 mmol) |
| tert-Butyllithium (1.7 M in pentane) | 32.4 mL (55.1 mmol) |
| Tetrahydrofuran (dried over 3A sieves) | 100 mL |
| Diphenylphosphinic chloride | 5.5 mL (28.8 mmol) |
| Magnesium bromide diethyl etherate | 14.2 g (55.0 mmol) | tert-Butyllithium was added dropwise over one hour to a solution of 3 in tetrahydrofuran at −78° C. After 30 minutes further magnesium bromide diethyl etherate was added and the reaction mixture allowed to reach room temperature. Diphenylphosphinic chloride was added and after two hours further the reaction was poured into 2N HCl (100 mL). The acid was extracted with methylene chloride (3×100 mL), the organic layers were combined, dried (MgSO$_4$) and the solvent was evaporated. The solid obtained was heated in ethyl acetate/hexanes (2:3), cooled and filtered to afford 4 as a white solid (5.0 g, 90%).

EXAMPLE 4

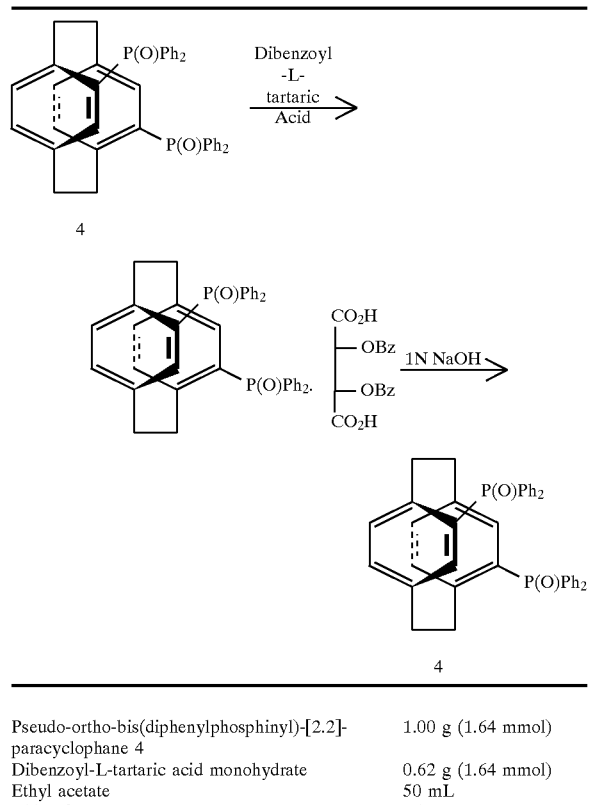

| | |
|---|---|
| Pseudo-ortho-bis(diphenylphosphinyl)-[2.2]-paracyclophane 4 | 1.00 g (1.64 mmol) |
| Dibenzoyl-L-tartaric acid monohydrate | 0.62 g (1.64 mmol) |
| Ethyl acetate | 50 mL |
| Chloroform | 75 mL |

A hot solution of dibenzoyl-L-tartaric acid monohydrate in ethyl acetate was slowly added to a solution of 4 in chloroform at 60° C. Approximately one third of the solvent was removed and the solution was cooled to room temperature. After 18 hours the solid was filtered, dissolved in chloroform (100 mL), washed with 1N aqueous sodium hydroxide (3×100 mL), dried (MgSO$_4$) and the solvent was evaporated to afford 4 as a white solid (380 mg; 76%; 100% ee, the enantiomeric excess being determined by supercritical fluid chromatography (SFC) using a chiral OD-H column).

EXAMPLE 5

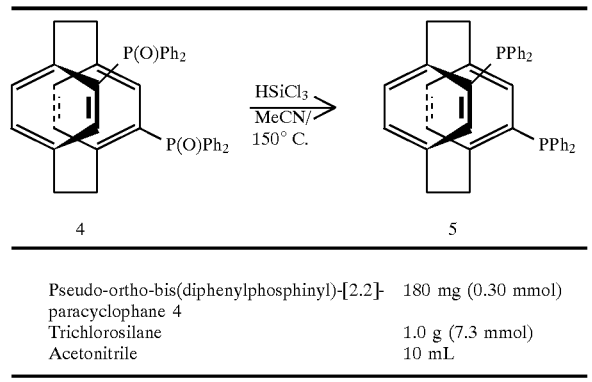

| | |
|---|---|
| Pseudo-ortho-bis(diphenylphosphinyl)-[2.2]-paracyclophane 4 | 180 mg (0.30 mmol) |
| Trichlorosilane | 1.0 g (7.3 mmol) |
| Acetonitrile | 10 mL |

Trichlorosilane was added to a slurry of 4 in acetonitrile and the reaction mixture was heated to 150° C. for 5 hours. 20% aqueous sodium hydroxide (100 mL) was added and the product was extracted into chloroform (3×50 mL). After drying (MgSO$_4$) the solvent was evaporated to afford pseudo-ortho-bis(diphenylphosphino)-[2.2]paracyclophane 5 as a white solid (140 mg; 82%).

EXAMPLE 6

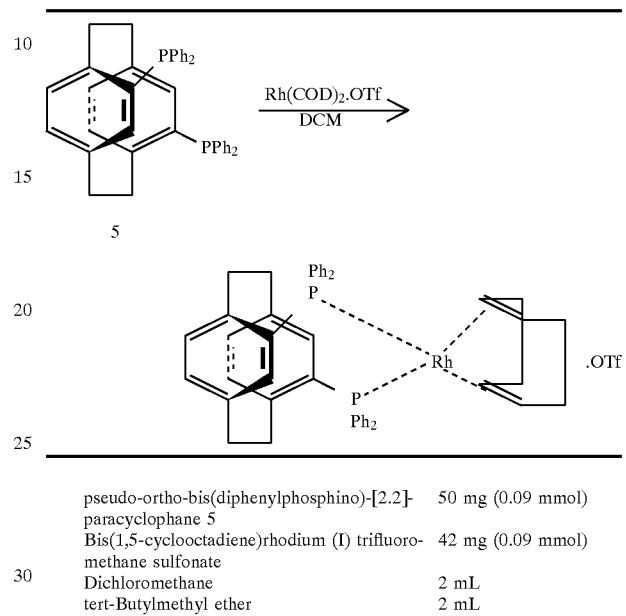

| | |
|---|---|
| pseudo-ortho-bis(diphenylphosphino)-[2.2]-paracyclophane 5 | 50 mg (0.09 mmol) |
| Bis(1,5-cyclooctadiene)rhodium (I) trifluoromethane sulfonate | 42 mg (0.09 mmol) |
| Dichloromethane | 2 mL |
| tert-Butylmethyl ether | 2 mL |

Dichloromethane was added to 5 and bis(1,5-cyclooctadiene)rhodium (I) trifluoromethane sulfonate and the solution stirred at room temperature for 1 hour. The dichloromethane was removed and tert-butylmethyl ether was added. The orange solid 6 was filtered and dried under nitrogen (80 mg; 87%).

EXAMPLE 7

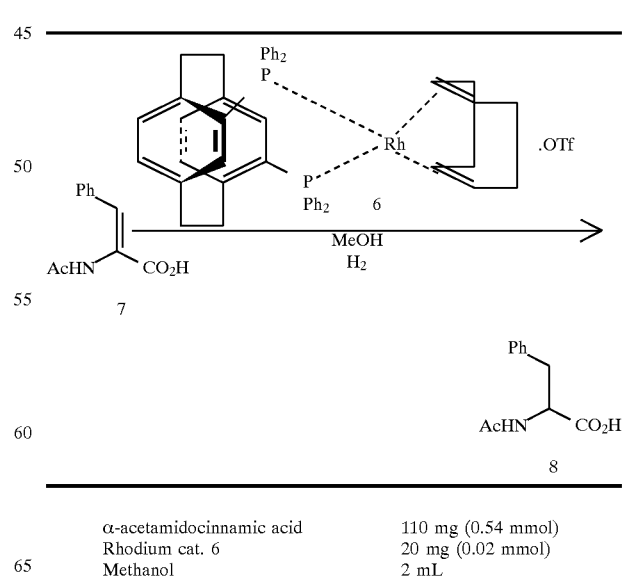

| | |
|---|---|
| α-acetamidocinnamic acid | 110 mg (0.54 mmol) |
| Rhodium cat. 6 | 20 mg (0.02 mmol) |
| Methanol | 2 mL |

6 was added to a degassed solution of α-acetamidocinnamic acid 7 in methanol and the reaction hydrogenated for 18 hours at room temperature. The enantiomer excess of the product was determined by supercritical fluid chromatography using a chiral ODH column. 8: $^1$H NMR: in agreement with literature values.

| H$_2$ pressure/psi | ee |
|---|---|
| 1000 | 52% |
| 60 | 65% |

EXAMPLE 8

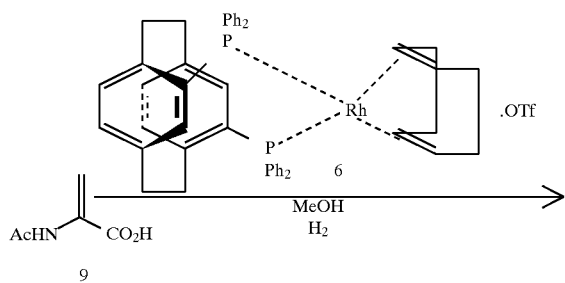

| α-acetamidoacrylic acid | 97 mg (0.54 mmol) |
|---|---|
| Rhodium cat. 6 | 18 mg (0.02 mmol) |
| Methanol | 20 mL |

6 was added to a degassed solution of α-acetamidoacrylic acid 9 in methanol and the reaction hydrogenated at 40 psi for 18 hours at room temperature. The enantiomer excess of the product was determined by derivatization to the corresponding methyl ester 12: the methanol was removed under reduced pressure and a solution of diazomethane added (ca. 0.6M in Et$_2$O). After 15 minutes the diethyl ether was removed and enantiomeric excess determined by gas chromatography using a Chiracil-Val III column (isothermal 105° C.; flow 10 cm/s; split ratio 140:1). ee=95% $^1$H NMR: in agreement with literature values.

EXAMPLE 9

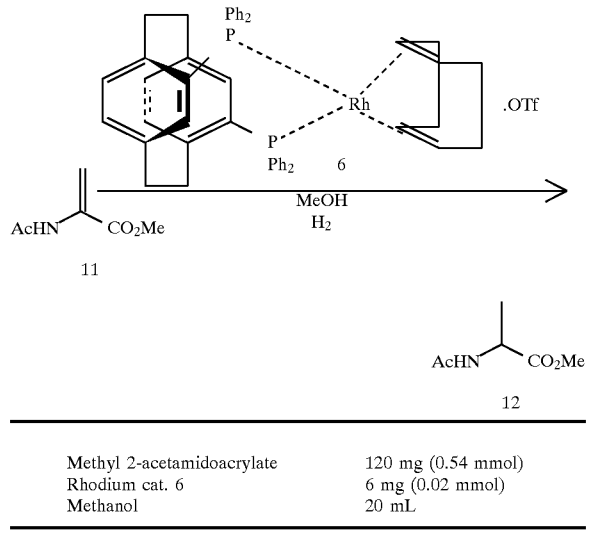

| Methyl 2-acetamidoacrylate | 120 mg (0.54 mmol) |
|---|---|
| Rhodium cat. 6 | 6 mg (0.02 mmol) |
| Methanol | 20 mL |

6 was added to a degassed solution of methyl 2-acetamidoacrylate 11 in methanol and the reaction hydrogenated at atmospheric presuure for 2 hours at room temperature. The enantiomer excess of the product was determined by gas chromatography using a Chiracil-Val III column (isothermal 105° C.; flow 10 cm/s; split ratio 140:1). ee=99.8% $^1$H NMR OF 12 in agreement with literature values.

EXAMPLE 10

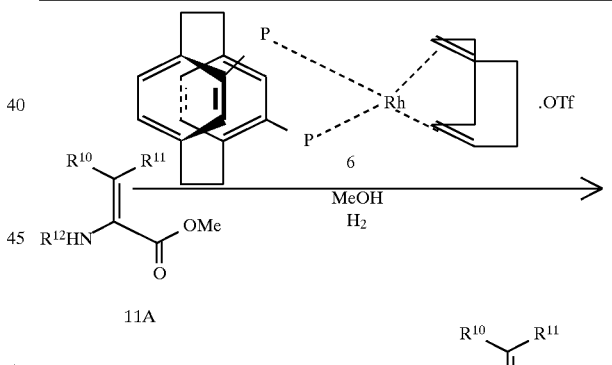

| Example | R$^{10}$ | R$^{11}$ | R$^{12}$ | ee (%) of 12A | Config |
|---|---|---|---|---|---|
| 1 | Ph | H | Ac | 98[a] (83[b]) | R |
| 2 | Me | H | Ac | 94[a] | R |
| 3 | Ph | H | Bz | 97[a] | R |
| 4 | H | H | Cbz | 91[a,c] (78[b]) | R |

[a]Precatalyst 6 was reduced at 23° C. prior to addition of substrate at −45° C.
[b]Precatalyst 6 was mixed with substrate prior to addition of substrate H$_2$ at 23° C.
[c]Conversion after 3 hours was 50%.

EXAMPLE 11

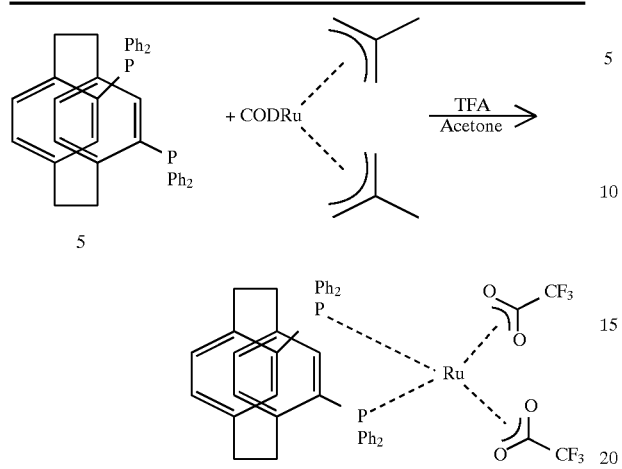

| | |
|---|---|
| (S)-PHANEPHOS (5) | 240 mg (0.42 mmol) |
| Bis(2-methylallyl)cycloocta-1,5-diene Ruthenium(II) | 120 mg (0.38 mmol) |
| Trifluroacetic acid | 58 μL |
| Acetone | 6 mL |

(S)-PHANEPHOS and Bis(2-methylallyl)cycloocta-1,5-diene Ruthenium(II) were charged to a Sclenk tube and dissolved in degassed acetone. Trifluroacetic acid was added and the reaction mixture was stirred for 24 hours. The solvent was removed, the residue was slurried in hexanes and filtered to afford (S)-PHANEPHOS Ruthenium bis trifluoroacetate as a light brown solid (280 mg; 74%).

EXAMPLE 12

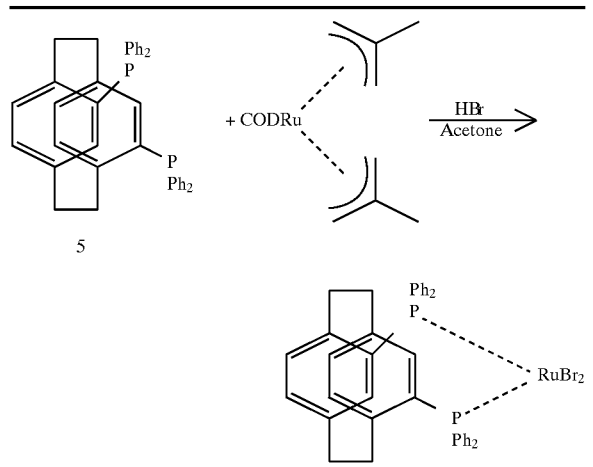

| | |
|---|---|
| (S)-PHANEPHOS (5) | 36 mg (0.06 mmol) |
| Bis(2-methylallyl)cycloocta-1,5-diene Ruthenium(II) | 18 mg (0.06 mmol) |
| HBr in MeOH (0.27 M) | 0.45 mL (0.12 mmol) |
| Acetone | 3 mL |

(S)-PHANEPHOS and Bis(2-methylallyl)cycloocta-1,5-diene Ruthenium(II) were charged to a Sclenk tube and dissolved in degassed acetone. HBr solution was added and the reaction mixture was stirred for 30 minutes. The solvent was removed and the light brown solid obtained used immediately in the hydrogenation reactions.

EXAMPLE 13

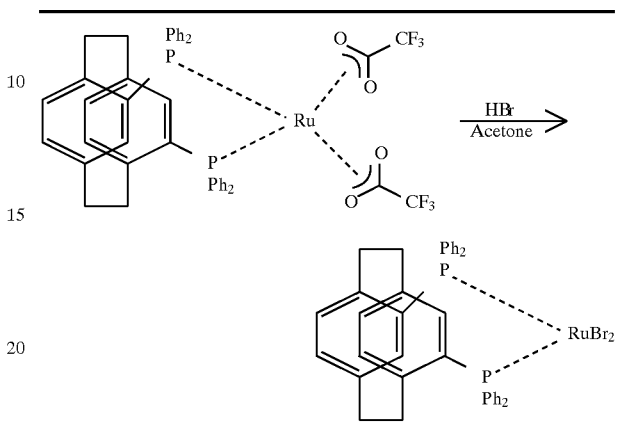

| | |
|---|---|
| (S)-PHANEPHOS Ruthenium bis trifluoroacetate | 30 mg (0.03 mmol) |
| HBr in MeOH (0.27 M) | 0.25 mL (0.07 mmol) |
| Acetone | 3 mL |

(S)-PHANEPHOS Ruthenium bis trifluoroacetate was charged to a Sclenk tube and dissolved in degassed acetone. HBr solution was added and the reaction mixture was stirred for 10 minutes. The solvent was removed and the light brown solid obtained used immediately in the hydrogenation reactions.

EXAMPLE 14

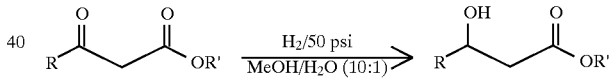

General Procedure:

The substrate (2.2 mmol) was dissolved in MeOH/water (2 mL; 10:1) and the solution degassed by three freeze/vacuum/purge cycles. The solution was charged to a Fisher-Porter tube and the Ruthenium catalyst added. The vessel was pressured to 50 psi after three vacuum/hydrogen purge cycles and stirred for 24 hours. Conversion was determined by 1H NMR to be 100% in each case

| R | R' | % ee | mol % Ru cat. used |
|---|---|---|---|
| Me | Me | 94 | 0.4 |
| Et | Me | 93 | 0.4 |
| Me | Et | 95 | 0.8 |
| Me | tBu | 94 | 0.4 |
| iPr | Et | 93 | 0.4 |
| ClCH$_2$ | Me | 77 | 0.8 |

EXAMPLE 15

Isolation of S pseudo-ortho-dibromo[2.2]paracyclophane 3

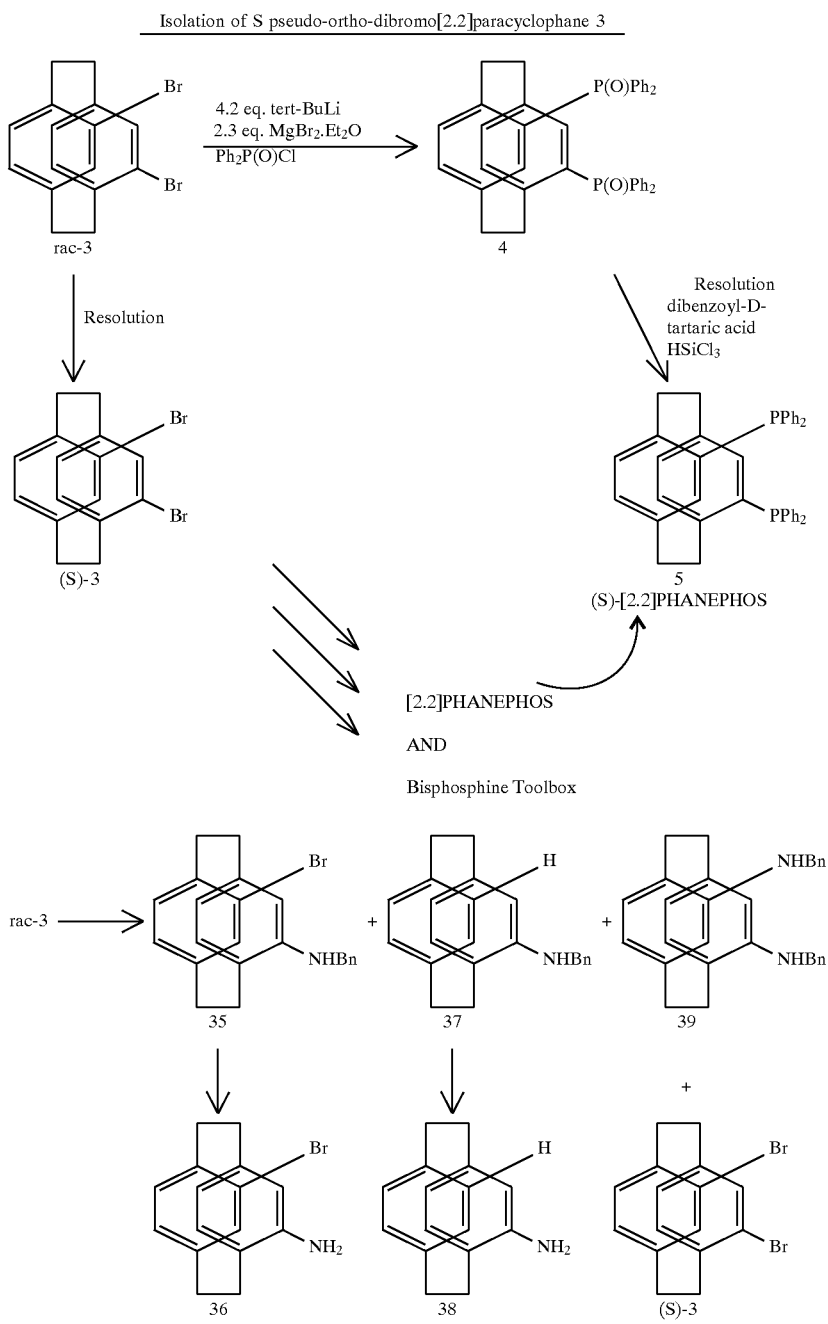

To a solution of 1.014 g (2.77 mmol) of rac-3 in 12 mL of thoroughly degassed toluene under $N_2$ in a Schlenk tube were added 1.06 g (11 mmol) NaOtBu followed by 1.39 g (4 mmol) Tl ($PF_6$), 48 mg (0.083 mmol) (S)-[2.2] PHANEPHOS and 29 mg (0.028 mmol) $Pd_2dba_3.CHCl_3$. The mixture was warmed to 50° C. for 10 min, when 0.61 mL (5.5 mmol) $BnNH_2$ were added. The reaction mixture was stirred at 50° C. for 10 hours and quenched by addition of 5 mL of MeOH and 50 mL of EtOAC. The crude reaction mixture was filtered through a bed of $SiO_2$ to remove the Tl salts (HIGHLY TOXIC). The filtrate is worked up in a standard way and the remaining 3 is isolated by $SiO_2$ chromatography as a white powder (0.214 g, 42% yield). The ee is determined to be 93% of (R)-3 using a Hewlett Packard Supercritical Fluid Chromatography system with a Chiralcel OD-H column. Separation conditions: 300 bar $CO_2$ with MeOH modifier gradient: 4 min at 4%, then ramping up to 36% within 32 min, flow 1 mL/min. Retention times (R)-3: 22.6 min, (S)-3: 25.5 min. The absolute configuration of (R)-3 and (S)-3 are known by correlation with the bisphosphine oxide of [2.2]PHANEPHOS, whose absolute configuration was determined by X-ray crystallography as a complex with dibenzoyl-D-tartaric acid.

TABLE 1

| Reaction Conditions | 2 h | 4 h | 6 h | 8 h |
|---|---|---|---|---|
| a Pd BINAP | 0.95 | 0.91 | 0.86 | 0.82 (5% ee, s = 2) |
| b Pd PHANEPHOS | 0.62 (34% ee, s = 4) | 0.39 (51% ee, s = 3) | 0.29 (70% ee, s = 3) | 0.23 (74% ee, s = 3) |
| c Pd PHANEPHOS 10 equiv. BnNH$_2$ | 0.64 (36% ee, s = 6) | 0.56 (42% ee, s = 5) | 0.25 (45% ee, s = 2) | 0.17 (47% ee, s = 2) |
| d Pd PHANEPHOS 2 equiv. Br- | 0.58 (42% ee, s = 6) | 0.39 (65% ee, s = 4) | 0.27 (76% ee, s = 3) | 0.19 (84% ee, s = 3) |
| e Pd PHANEPHOS 10 equiv. NaOtBu | 0.48 (41% ee, s = 3) | 0.32 (64% ee, s = 3) | 0.23 (74% ee, s = 3) | 0.12 (83% ee, s = 3) |
| f Pd PHANEPHOS 2 equiv. Tl PF$_6$ | 0.84 (18% ee, s = 42) | 0.70 (32% ee, s = 10) | 0.66 (41% ee, s = 13) | 0.63 (45% ee, s = 12) |

All reactions were run in a Schlenk tube under N$_2$ with catalyst prepared from 1 mol% of Pd$_2$dba$_3$.CHCl$_3$ and 3 mol % of bisphosphine in thoroughly degassed toluene at 50° C. at 0.2M concentration. All reactions used 2 equiv. of BnNH$_2$ (except c) and 3 equiv. of NaOtBu (except e). Additionally, 2 equiv. of CH$_3$(CH2)$_{17}$NMe$_3$ Br was added to d, and 2 equiv of Tl PF$_6$ was added to f. The reactions were quantified using HPLC intergration of the reaction mixture containing 1-methylnaphthaline as internal standard.

Resolution of Pseudo-ortho-dibromo[2.2]paracyclophane (3)

Rac-Pseudo-ortho-dibromo[2.2]paracyclophane 3 (400 mg) was dissolved in ethanol and loaded onto a column (100 mm dia. ×300 mm length) prepacked with cellulose triacetate (15–25 μm mesh) as adsorbent. The column was eluted with ethanol and 150 mL fractions collected. The separation was monitored by supercritical fluid chromatography using a Chiracell OD-(H) column. The fractions were evaporated to afford enantiomerically pure R and S pseudo-ortho-dibromo[2.2]paracyclophane 3 180 mg and 160 mg respectively.

EXAMPLE 16

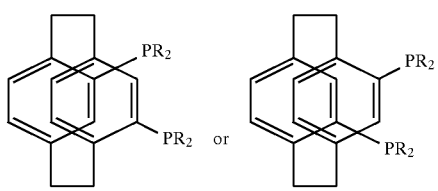

The preparation of the [2,2]PHANEPHOS analogous compounds was undertaken in an similiar fashion as the preparation of [2,2]PHANEPHOS. The synthesis started with optically pure pseudoortho dibromide, followed by a metalation with BuLi and an optional transmetalation to the Grignard reagent with MgBr$_2$ followed by a quench with R$_2$POCl. Subsequent reduction lead to the bisphosphine ligand. Alternatively, the ligands were prepared from the racemic pseudo-ortho dibromide following the same synthetic sequence and resolving at the stage of the phosphine-oxide.

The following ligands were prepared:

R
- 4-methyl-phenyl
- 4-methoxy-phenyl
- 4-fluoro-phenyl
- 3,5-bis-(trifluoromethyl)phenyl
- 3,5-dimethyl-phenyl
- 3,5-dimethyl-4-methoxy-phenyl
- cyclohexyl
- isopropyl The compounds were obtained in 75–86% yield.

EXAMPLE 17

| Pyrazine-2-tert-butylcarboxamide 13 | 15.00 g (0.084 mol) |
|---|---|
| Di-tert-butyl dicarbonate | 21.9 g (0.1 mol) |
| 10% Pd/C | |
| EtOH | 150 mL |

To a solution of 13 in EtOH was added Pd/C. The reaction was hydrogenated in a Parr shaker at 40° C. and 35° C. for 18 h. The catalyst was filtered off and the filter cake was washed with 100 mL of EtOH. The solvent was switched to EtOAc (ca. 100 mL), and on seeding 14 precipitated as white crystals (17.3 g, 73% yield). $^{13}$C NMR (CDCl$_3$): 165.1, 155.7, 130.0, 129.8, 81.3, 50.5, 41.5, 40.5, 29.2, 28.3.

EXAMPLE 18

Into a slurry of 14 (18.58 g, 0.066 Mol) in 200 mL EtOAc was bubbled an excess of HCl gas at 10°–15° C. The resulting slurry was aged overnight at 20° C. and filtered. The filtrate was washed with EtOAc and hexane and dried in a N$_2$ stream to give 15.2HCl (16.42 g, 98%).

EXAMPLE 19

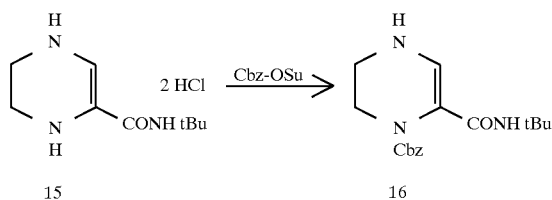

A slurry of 15.2HCl (12.09 g; 0.047 Mol) in 160 mL EtOAc was degassed in a $N_2$ stream and cooled to 5° C. $Et_3N$ (16.5 mL, 0.12 Mol) and N-(benzyloxycarbonyloxy) succinimide (12.35 g, 0.05 Mol) were added and the reaction mixture was stirred at 22° C. overnight. The reaction mixture was washed with $H_2O$, 5% citric acid, 5% $NaHCO_3$ and brine. After drying ($MgSO_4$), the organic phase was filtered through a plug of $SiO_2$ and evaporated. Crystallization from EtOAc/cyclohexane 10/90 gave 16 (9.39 g, 63% yield). Anal. Calcd for $C_{17}H_{23}N_3O_3$: C, 64.33; H, 7.30; N, 13.24. Found: C, 64.23; H, 7.31; N, 13.17. mp 161°–162° C.

EXAMPLE 20

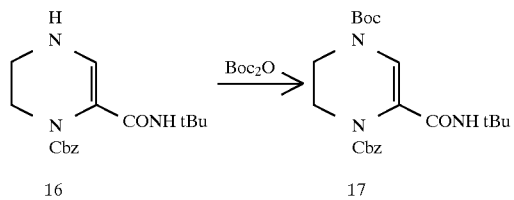

To a slurry of 16 (18.59 g, 0.059 Mol) in 120 mL isopropyl acetate was added $Boc_2O$ (20 mL, 0.12 Mol) and diisopropylethylamine (1 mL). On heating to reflux the reaction mixture turned homogeneous and was refluxed for 18 h. The reaction mixture was evaporated and chromatographed ($SiO_2$, EtOAc/hexane 50/50) to give 17 as an oil (24.5 g, 100%). Crystallization from cyclohexane/isopropyl acetate 10/1 gave 17 as a white solid. Anal. Calcd for $C_{22}H_{31}N_3O_5$: C, 63.29; H, 7.48; N, 10.06. Found: C, 63.30; H, 7.40; N, 9.94. mp. 99°–100° C.

EXAMPLE 21

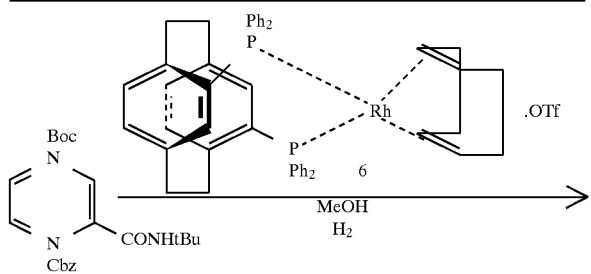

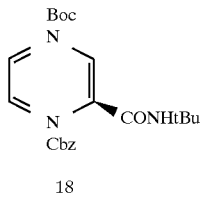

| Boc—Cbz-Tetrahydropyrazine-tert-butyl-carboamide 17 | 433 mg (1.04 mmol) |
|---|---|
| Rhodium cat. 6 | 20 mg (0.02 mmol) |
| Methanol | 10 mL |

Catalyst 6 was added to a degassed solution of 17 in methanol and the reaction hydrogenated at 40 psi for 18 hours at 40° C. in a Parr hydrogenation apparatus. The enantiomeric excess of the product was determined by supercritical fluid chromatography. 65% ee. $^1H$ NMR of 18 was in agreement with literature values.

EXAMPLE 22

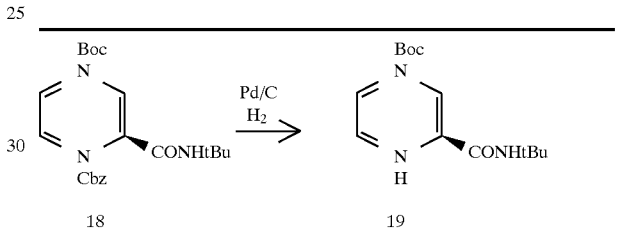

| (S)—Cbz—Boc-Piperazine-2-tert-butyl-carboxamide 18 | 1.055 g (2.52 mmol) |
|---|---|
| Pearlman's catalyst | 0.157 g |
| MeOH | 16 mL |

To a solution of 18 in MeOH was added Pearlman's catalyst. The solution was hydrogenated at 40 psi and 22° C. TLC (EtOAc/hex 50/50) indicated completion of the reaction. The catalyst was removed by filtration and the filtrate was evaporated. Cyclohexane (5 mL) was added and the oil was dissolved by heating. On cooling 19 precipitated and was filtered to give after drying 0.7 g (99%) of 19 as a white powder. [alpha] 589=22° (c=0.2, MeOH), m.p. 107° C.; $^{13}C$ NMR ($CDCl_3$) 170.1, 154.5, 79.8, 58.7, 50.6, 46.6, 43.6, 43.4, 28.6, 28.3.

EXAMPLE 23

| A. Conversion of Indene Oxide to Cis-1-Amino-2-Indanol | | | |
|---|---|---|---|
| Materials | Mol. Wt. | Grams or ml | Millimoles |
| Indene oxide | 132 | 1 ml | 8.33 |
| Acetonitrile | 41 | 10 ml | 244 |
| Water | 18 | 2.15 ml | 119.4 |
| Conc. $H_2SO_4$ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 mmoles) dissolved in 10 ml acetonitrile was added 0.15 ml water (8.33 mmoles). The mixture was cooled to 0°–5° in an ice bath. Concentrated sulfuric acid was added dropwise while maintaining the batch temperature below 10°. When all the acid was added and the temperature was allowed to rise to 20°–250°. The clear solution was aged for 30 minutes.

To this mixture was added 2 ml of water and the solution heated for 30 minutes. When the methyl oxazoline was completely coverted to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above, 2 re-acylation occurs and the yield of amino indanol is reduced. The white solid ($K_2SO_4$) was removed by filtration.

Dowex resin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N $NH_3$ in methanol and the slurry stirred at room temperature for 30 minutes. The resin was again collected by filtration and the methanol/$NH_3$ saved. Another charge of 1N $NH_3$/MeOH (20 ml) was added and the resin re-slurried. After removal of the resin the methanol/$NH_3$ solutions of the amino indanol were combined and concentrated to remove the $NH_3$. Analysis of the final MeOH solution shows 1.0 g (81% yield) cis-1-amino-2-indanol ready for the tartaric acid resolving agent.

B. Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

C. Preparation of (1S, 2R)-indene oxide

The substrate, (1S, 2R)-indene oxide is prepared according to the method described by D. J. O'Donnell, et al., *J. Organic Chemistry*, 43, 4540 (1978), herein incorporated by reference for these purposes.

D. Preparation of cis-1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis 1-amino-2-indanol.

E. Preparation of 1S-amino-2R-indanol (1,S, 2R)-indene oxide (85% ee,) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h then cooled to room temperature. Chlorobenzene (1000 mL) was added, the mixture stirred, the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee, 160 g).

F. Preparation of 1S-amino-2R-indanol (1S, 2R)-indene oxide (85% ee,) (250 g, 0.185 mole) was dissolved in chlorobenzene (300 mL) and heptanes (1200 mL) and slowly added to a solution of fuming sulfuric acid (21% $SO_3$, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h, then cooled to room temperature. Chlorobenzene (1000 mL) was added, the mixture stirred, the organic phase separated. The remaining aqueous phase containing 1S-amino, 2R-indanol (85% ee, 205 g, 74%) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee, 205 g).

Alternatively, the remaining aqueous phase containing 1S-amino-2R-indanol (85% ee, 205 g, 74%) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the amino-indanol.

G. Use of benzonitrile

Indene oxide (5 g) was dissolved in benzonitrile (50 mL) at 25° C. and sulfuric acid (98%, 2.25 mL) was added. The mixture was diluted with 5M aqueous sodium hydroxide solution (50 mL) and extracted with methylene chloride. The organic extracts were concentrated in vacuo to give 5.03 g of oxazoline.

H. Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate (88 g).

I. Preparation of 1S-Amino-2R-indanol

1S-Amino, 2R-indanol L-tartaric acid salt methanol solvate (88 g) was dissolved in water (180 mL) and heated to 55°–60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure, 37 g).

J. Conversion of 1,2 indanol to cis-1-amino-2-indanol

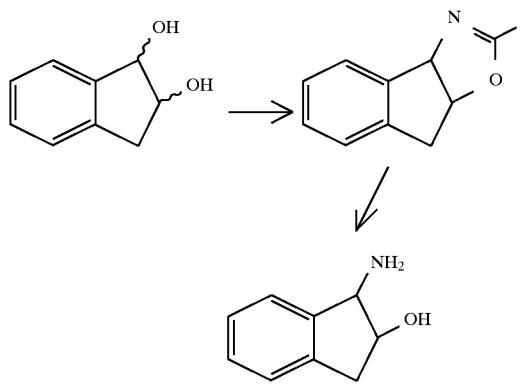

| Materials | Mol Wt | Grams or ml | Millimoles |
|---|---|---|---|
| 1,2 indane diol | 150 | 300 mg | 2 |
| acetonitrile | 41 | 2.5 ml | 47.3 |
| water | 18 | 0.04 ml | 2 |
| sulfuric acid | 98 | 0.22 ml | 4 |
| 5 N KOH | 57 | 1.6 ml | 8.0 |
| Dowex | | 10 ml | |
| 50 × 4 (H+) | | | |
| methanol (1 m NH$_3$) | | 30 ml | |

To 300 mg indane diol dissolved in 3 ml of acetonitrile containing 0.04 ml water was added dropwise at 0°–10° C. a volume of 0.22 ml of concentrated H$_2$SO$_4$. After the addition was complete the ice bath was removed and the batch warmed to room temperature. After a 30 minute age the clear solution was sampled for Ic assay (dilx 500). When all the glycol was consumed, the solution was treated further with water and heated to reflux on a steam bath to hydrolyze the oxazoline.

When Ic analysis showed hydrolysis complete, 1.6 ml 5N KOH was added to neutralize the sulfuric acid. Potassium sulfate was filtered from the solution.

The filtrate was assayed for cis amino indanol and contained 196 mg (66% of theory, which is also 75% corrected for unreacted starting material). The solution was passed over 10 ml of Dowex 50×4 (H+). The column spents were checked for product. All the amino indanol was adsorbed. After washing the resin with methanol, the product was eluted with a solution 1M in NH$_3$ (dry). The ammoniacal methanol was concentrated to remove the NH$_3$ and the final solution of amino-indanol ready for resolution was assayed. (175 mg, or 59% of theory when uncorrected for unreacted glycol).

K. Preparation of Indanol Reactants

Compounds (±)-trans-2-bromo-1-indanol were prepared by methods of S. M. Sutter et al., *J. Am. Chem. Soc.*, 62, 3473 (1940); and D. R. Dalton et al., *J. C. S. Chem. Commun.*, 591 (1966). Compounds (+)-trans-2-bromo-1-indanol and cis- and trans-1,2-indandiols were prepared by the methods of M. Imuta et al., *J. Org. Chem.*, 43, 4540 (1978).

L. Preparation of cis-1-amino-2-indanol from trans-2-bromo-1-indanol

Trans-2-bromo-1-indanol (10 g, 46.9 mmole diluted in 100 mL of acetonitrile containing 0.8 mL water) was cooled to –5° C. and concentrated sulfuric acid (5.2 mL) was added. The mixture was aged for 1 h, then 5M aqueous potassium hydroxide was added to adjust the pH to 11. The reaction mixture was filtered, removing the potassium sulfate salts. The aqueous acetonitrile filtrate was adjusted to pH less than 2 with sulfuric acid and heated to 80°–100° C., removing acetonitrile by distillation to provide an aqueous solution of cis-1-amino-indanol. The solution was concentrated to a volume of 20 mL, then adjusted to pH 12.5 with potassium hydroxide. The product crystallizes, was filtered and dried in vacuo to provide cis-1-amino-2-indanol (4.25 g).

M. Preparation of cis-1S-amino-2R-indanol from cis-(1S, 2R)-indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5M potassium hydroxide (1.6 mL) was added to adjust the pH to more than 11 and the resulting solid (potassium sulfate) removed by filtration to provide an aqueous solution of the cis-1S-amino-2R-indanol (0.79 g, 66% yield).

N. Preparation of cis-1-amino-2-indanol from trans-1,2-indandiol

Trans-1,2-indandiol (1.5 g) was dissolved in acetonitrile (25 mL) cooled to 0° C., and concentrated sulfuric acid (1.1 mL) was added. The mixture was gradually warmed to 20° C. and aged to 3 hours. Water (2 mL) was added and the mixture heated to reflux. Concentrated aqueous sodium hydroxide was added to adjust the pH to 12. The resulting solid was removed by filtration to provide an aqueous acetonitrile solution of cis-1-amino-2-indanol (1.02 g, 63% yield).

O. Preparation of cis-1-amino-2-indanol from cis-1,2-indandiol

Cis-1,2-indandiol (1.0 g) was dissolved in acetonitrile (20 mL), cooled to –40° C., and fuming sulfuric acid (21% SO$_3$, 0.8 mL) was added. The mixture was aged for 1 hour with gradual warming to 0° C. Water was added and the mixture heated to 80° C. for 1 hour to provide an aqueous solution of cis-1-amino-2-indanol.

EXAMPLE 24

Preparation of Acetonide 22

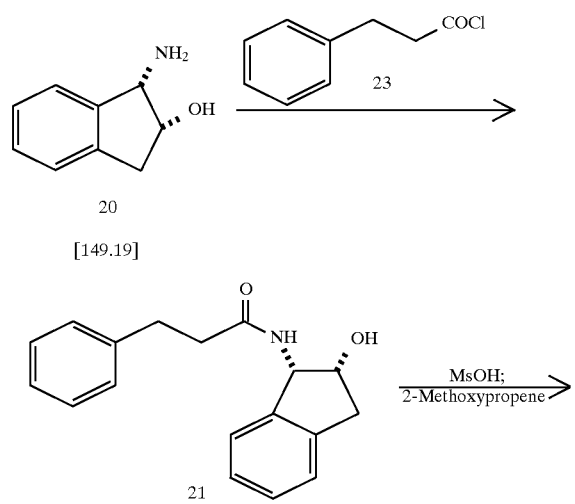

-continued

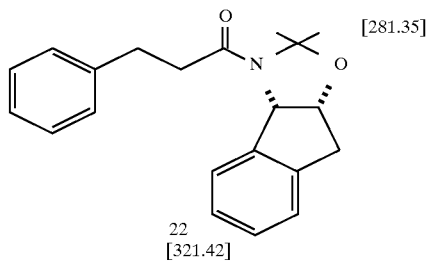

| (−)-cis-1-aminoindan-2-ol (20) | 900 g | 6.02 mol |
| --- | --- | --- |
| (99.7 wgt. %, 99.9 area %, >99.5% ee) | | |
| sodium carbonate monohydrate | 760 g | 6.13 mol |
| diethoxymethane (DEM) | 56.3 L | |
| 3-phenylpropionyl chloride (23) | 1.05 kg | 6.23 mol |
| methanesulfonic acid (MSA) | 18.6 g | 0.19 mol |
| 2-methoxypropene (95% by GC) | 1.28 L | 13.3 mol |
| 5% aqueous NaHCO$_3$ | 10.8 L | |
| water | 26.2 L | |

A slurry mixture consisting of (−)-cis-1-aminoindan-2-ol (20, 900 g, 6.02 mol) in 40 L of DEM and aqueous sodium carbonate solution (760 g, 6.13 mol, of Na$_2$CO$_3$.H$_2$O in 6.4 L of water) in a 100 L reactor with four inlets, equipped with a thermocouple probe, mechanical stirrer, and a nitrogen inlet adapter and bubbler, was heated to 46°–47° C. and aged for 15 minutes. The reaction mixture was heated to 46°–47° C. and aged for 15 minutes to insure dissolution of the solids. The aqueous phase had a pH of 11.5. Neat 3-phenylpropionyl chloride 23 (1.05 kg, 6.23 mol) was added over 2 h between 47° C. to 59° C. The internal temperature increased from 47° C. to 59° C. during the addition of 23; the hydroxyamide 21 crystallized out of solution during the acid chloride addition. After the addition was complete, the reaction mixture was aged at 59° C. for 0.5 h and then warmed to 72° C. to insure dissolution of the solids. The temperature was increased to 72° C. to dissolve the hydroxyamide so that a homogeneous sample can be obtained for HPLC assay and to simplify the phase cuts. Progress of the reaction was monitored by HPLC analysis: 60:40 Acetonitrile/5.0 mM of each KH$_2$PO$_4$ and K$_2$HPO$_4$. Approximate retention times:

| retention time (min.) | identity |
| --- | --- |
| 4.1 | hydroxy amide 21 |
| 6.3 | cis-aminoindanol 20 |
| 12.5 | ester amide by product |

After complete acid chloride addition and 0.5 h age at 72° C., the HPLC assay of the reaction mixture showed ~0.6 area % of 20, ~0.2 area % of ester amide by product and 98.7 area % of hydroxyamide. The hydroxy amide 21 was not efficiently rejected in the isolation of acetonide 22. The aqueous phase was separated and the organic phase was washed twice with 4.5 L of water. The washed organic phase was concentrated and dried via atmospheric azeotropic distillation. The initial volume of ~40 L was concentrated to 27 L. A total of 16 L of fresh DEM was charged to the still and the batch was concentrated at 88° C. to 89° C. to 40 L.

The dried DEM slurry of hydroxyamide 21 was treated with 1.28 L of 2-methoxypropene followed by 18.6 g of MSA at 30° C. The addition of MSA in absence of 2-methoxypropene resulted in the formation of an amine ester. This impurity reconverts to hydroxyamide 21 during the basic work up at the end of the acetonide formation. The pH of 1.0 mL sample diluted with 1.0 mL water was found to be 2.8–3.0. The resulting mixture was aged at 39° C. to 40° C. for 3 h. The acetonide formation was monitored by HPLC analysis using the same conditions as described above in this example. Approximate retention times:

| retention time (min.) | identity |
| --- | --- |
| 4.1 | hydroxy amide 21 |
| 6.9 | methylene ketal impurity |
| 9.0 | acetonide 22 |
| 12.5 | ester amide by product |

The mixture was aged at 38°–40° C. until 21 is <0.4 A %. A typical HPLC area % profile is as follows: 0.4 area % of hydroxyamide 21, 96.9 area % of acetonide 22, 0.2 area % of ester amide by product, 1.1 area % of methylene ketal impurity. The reaction mixture was cooled to 24° C. and quenched with 10.8 L of 5% aqueous sodium bicarbonate solution. The aqueous phase was separated and the organic phase was washed twice with 10.8 L of water. The pH of the water wash was 7.6. If the pH was too low, the acetonide group could be hydrolyzed back to give the hydroxyamide 21. The washed organic phase (34.2 L) was concentrated via atmospheric distillation at 78° C. to 80° C. to final volume of 3.5 L. The acetonide concentration was made ~525 g/L to minimize isolation losses. The hot DEM solution of 22 was allowed to cool to 57° C., seeded with 0.5 g of 22 and further cooled to 0° C. and aged for 0.5 h. The batch started to crystallize out of solution between 53° C. to 55° C. The product was isolated by filtration and the wet cake was washed with cold (0° C.) DEM (300 mL). The washed cake was dried under vacuum (26" of Hg) at 30° C. to afford 1.74 kg of acetonide 22 (90%, >99.5 area % by HPLC).

EXAMPLE 25

Preparation of Acetonide 22 from (20- tartaric acid) salt

| (−)-cis-1-aminoindan-2-ol tartrate salt | 100 g | 297 mmol |
| --- | --- | --- |
| methanol solvate (44.3 wt. % of free base 22) | | |
| sodium carbonate monohydrate | 63.76 g | 514 mmol |
| diethoxymethane (DEM) | 2.83 L | |
| 3-phenylpropionyl chloride (23) | 52.7 g | 312 mol |
| methanesulfonic acid (MSA) | 0.95 g | 9.86 mmol |
| 2-methoxypropene (95% by GC) | 63 mL | 658 mmol |
| 5% aqueous NaHCO$_3$ | 520 mL | |
| water | 1.32 L | |

A slurry mixture consisting of (−) 20.tartrate salt methanol solvate (100 g, 44.3 g of free base, 297 mmol) in 2.0 L of (DEM) and aqueous sodium carbonate solution (63.8 g, 514 mmol, of Na$_2$CO$_3$.H$_2$O in 316 mL of water) in a 5.0 L reactor with four inlets, equipped with a thermocouple probe, mechanical stirrer, and a nitrogen inlet adapter and bubbler, was heated to 50° C. Heating the reaction mixture to 60° C. did not dissolve all the solids. Neat 3-phenylpropionyl chloride 23 (52.7 g, 312 mmol) was added over 30 min at 50° C. and the mixture was aged at 50° C. for 15 min. Progress of the reaction is monitored by HPLC analysis: 60:40 Acetonitrile/5.0 mM of each KH$_2$PO$_4$ and K$_2$HPO$_4$, 1.0 mL/min. Approximate retention times:

| retention time (min.) | identity |
|---|---|
| 4.1 | hydroxy amide 21 |
| 6.3 | cis-aminoindanol 20 |
| 12.5 | ester amide by product |

After complete acid chloride addition and 15 min. age at 50° C., the HPLC assay of the slurry mixture showed ~0.1 area % of 21. After this point, the reaction mixture was heated to 75° C.

The temperature was increased to 75° C. to dissolve the hydroxyamide 21 in DEM and simplify the phase separations. The aqueous phase was separated and the organic phase was washed twice with water (250 mL). The sodium tartrate was removed in the aqueous phase. The first aqueous cut had a pH of 8.98. The pH of the two water washes were 9.1 and 8.1, respectively. The washed organic phase was concentrated and dried via atmospheric distillation. Approximately 1.0 L of distillate was collected and 750 mL of fresh DEM was charged back to the distillation pot. The atmospheric distillation was continued until another 350 mL of distillate was collected. The solution KF was 93 mg/L. The dried DEM solution was cooled to 30° C. and treated with 63 mL of 2-methoxypropene followed by 0.95 g of MSA. The pH of 1.0 mL sample diluted with 1.0 mL water is 3.2. The reaction mixture was aged at 35°–42° C. for 2 h. The acetonide formation was monitored by HPLC analysis using the same conditions as described above in this Example. Approximate retention times: same as above. The mixture is aged at 38°–40° C. until 21 is ≦0.7 A %. A typical HPLC area % profile is as follows: 0.4 area % of hydroxy amide, 96.9 area % of acetonide 22, 0.2 area % of ester amide by product, 1.1 area % of methylene ketal impurity. The reaction mixture was cooled to 20° C., filtered to remove the cloudy appearance and quenched with 520 mL of 5% aqueous sodium bicarbonate solution. The aqueous phase was separated and the organic phase was washed with 500 mL of water. The pH of the water wash is 7.4. The washed organic phase (~2.0 L) was concentrated via atmospheric distillation at 78° C. to 80° C. to final volume of 1.0 L. The acetonide concentration in the isolation was maintained at ~525 g/L to minimize isolation losses. The hot DEM solution of 22 was allowed to cool to 50°–52° C., seeded with 100 mg of product and further cooled to 5° C. and aged for 20 min. The batch started to crystallize out of solution at 50° C. The product was isolated by filtration and the wet cake was washed with cold (0° C.) DEM (2×40 mL). The washed cake was dried under vacuum (26" of Hg) at 30° C. to afford 83.8 g of acetonide 22 (87.9%, >99.5 area % by HPLC).

EXAMPLE 26

| Preparation of Acetonide 22 (Isopropyl Acetate Solvent) | | |
|---|---|---|
| (−)-cis-1-aminoindan-2-ol (20) (98.5 wgt. %) | 80 g | 535 mmol |
| isopropyl acetate (IPAC) | 1.2 L | |
| water | 560 mL | |
| 5N sodium hydroxide | 116 mL | 580 mmol |
| 3-phenylpropionyl chloride (23) | 90.8 g | 539 mmol |
| methanesulfonic acid (MSA) | 1.1 mL | 17.0 mmol |
| 2-methoxypropene (95% by GC) | 119 mL | 1.24 mol |
| 5% aqueous NaHCO₃ | 950 mL | |
| water | 400 mL | |
| methyl cyclohexane | 2.25 L | |

A mixture of of (−)-cis-1-aminoindan-2-ol 20 (80 g, 535 mmol) in 1.2 L of IPAC and 560 mL of water was treated with 23 (90.8 g, 539 mmol) while the pH was maintained between 8.0–10.5 at 70°–72° C. with 5N sodium hydroxide (116 mL, 580 mmol).

Progress of the reaction was monitored by HPLC analysis: 60:40 Acetonitrile/5.0 mM of each $KH_2PO_4$ and $K_2HPO_4$. Approximate retention times:

| retention time (min.) | identity |
|---|---|
| 4.1 | hydroxy amide 21 |
| 6.3 | cis-aminoindanol 20 |
| 12.5 | ester amide by product |

At the end of the reaction, the aqueous phase was separated and the organic phase was washed with water (400 mL) at 72° C.–73° C. The pH of the aqueous phase and the aqueous wash was 8.1 and 7.9, respectively. The wet IPAC phase was dried via atmospheric distillation. A total of 3.0 L of IPAc was charged to lower the batch KF to <100 mg/L. The final volume is ~1.60 L. The resulting IPAC slurry of hydroxyamide 21 was treated with 2-methoxypropene (119 mL, 1.24 mol) followed by MSA (1.1 mL, 3.2 mole %) at 35° C.–38° C. for 4.5 h. The acetonide formation was monitored by HPLC analysis using the same conditions as described above. The mixture was aged at 38°–40° C. until 21 is <0.4 area %. The reaction was filtered to remove the hazy precipitate and the filtrate was quenched into cold sodium bicarbonate solution (950 mL) over 15 min. The aqueous phase was separated and the organic phase was washed with water (400 mL). The sodium bicarbonate solution was cooled to 0° C.–5° C. The pH of the aqueous phase and the aqueous wash was found to be 7.5 and 7.9, respectively. Atmospheric distillation was carried out while the solvent was switched to methylcyclohexane from IPAC. The initial volume before atmospheric concentration was 1.65 L. A total of 1.5 L of methylcyclohexane was added to complete the solvent switch to methylcyclohexane from IPAC. The batch temperature at the end of the solvent switch was 101° C. and the final batch volume was ~900 mL. The batch was heated to 65° C.–70° C. to insure dissolution of the solids, then cooled to 55° C., seeded with the product and cooled to 0° C. The mixture was aged at 0° C. for 15 min and the product was isolated by filtration and washed with cold methylcyclohexane (200 ml). The washed cake was dried under vacuum (26" of Hg) at 30° C. to afford 151 g of acetonide 22 (87.5%, >99.5 area % by HPLC).

EXAMPLE 27

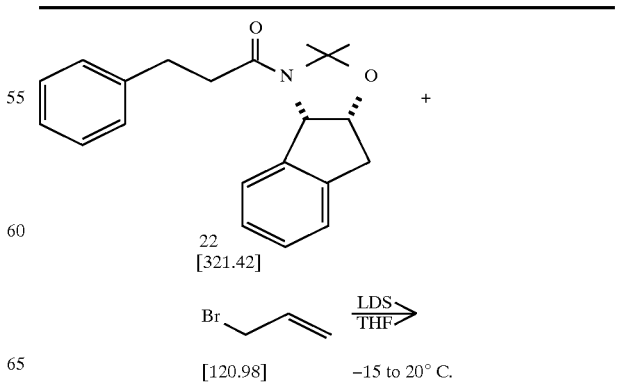

-continued

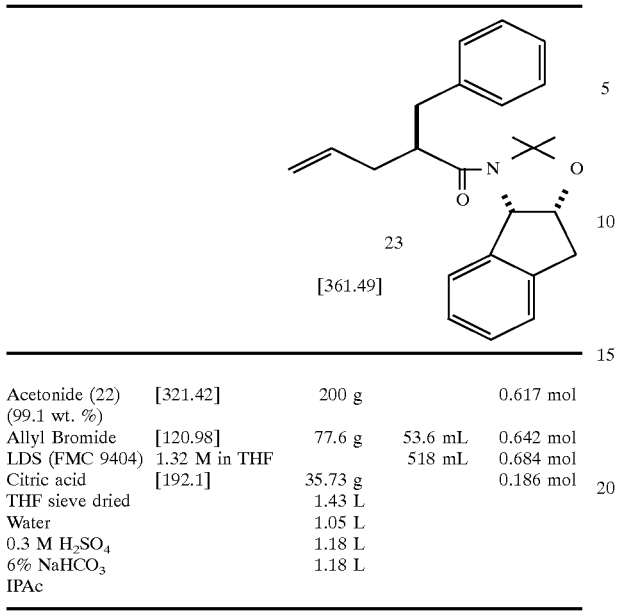

| Acetonide (22) (99.1 wt. %) | [321.42] | 200 g | | 0.617 mol |
| --- | --- | --- | --- | --- |
| Allyl Bromide | [120.98] | 77.6 g | 53.6 mL | 0.642 mol |
| LDS (FMC 9404) | 1.32 M in THF | | 518 mL | 0.684 mol |
| Citric acid | [192.1] | 35.73 g | | 0.186 mol |
| THF sieve dried | | 1.43 L | | |
| Water | | 1.05 L | | |
| 0.3 M H₂SO₄ | | 1.18 L | | |
| 6% NaHCO₃ | | 1.18 L | | |
| IPAc | | | | |

The crystalline acetonide 22 (200 g, 0.622 mol, 99.1 wt. %) was dissolved in 1.25 L sieve dried THF (KF=11 mg/L) under nitrogen atmosphere at 25° C. with mechanical stirring. The resulting KF of the solution at this point was 40 mg/L. The solution was subjected to three alternating vacuum/nitrogen purge cycles to thoroughly degas the solution of dissolved oxygen.

Allyl bromide was added to the THF solution. The resulting KF was 75 mg/L. Typical complete conversion (>99.5%) has been obtained with pre-LDS solution KF levels of 200 mg/L with the 10% base excess present in this procedure. The solution was then cooled to −20° C. A THF solution of lithium hexamethyldisilazide (LDS, 1.32M) was added to the allyl bromide/22 solution at such a rate as to maintain the reaction temperature at −20° C. The LDS addition took 30 min. The mixture was aged at −15° to −20° C. and quenched when the conversion was >99%. Analysis of the reaction was carried out by HPLC. Approximate retention times: hydroxyacetonide by product=5.3 min, ethyl benzene=5.6 min, acetonide 22=6.6 min; allyl acetonide 23=11.8 min; epi-23=13.3 min. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°–15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by ¹H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86 L.

The pH of the mixture after the three aqueous washes was 6.5, 1.3 and 8.5, respectively. HPLC analysis of the mixture at this point indicated 93–94% assay yield for 23. The ratio of the desired 23:epi-23 was 96:4 by HPLC (same conditions as above). GC analysis at this point indicated that the hexamethyldisilazane by-product had been completely removed in the workup.

EXAMPLE 28

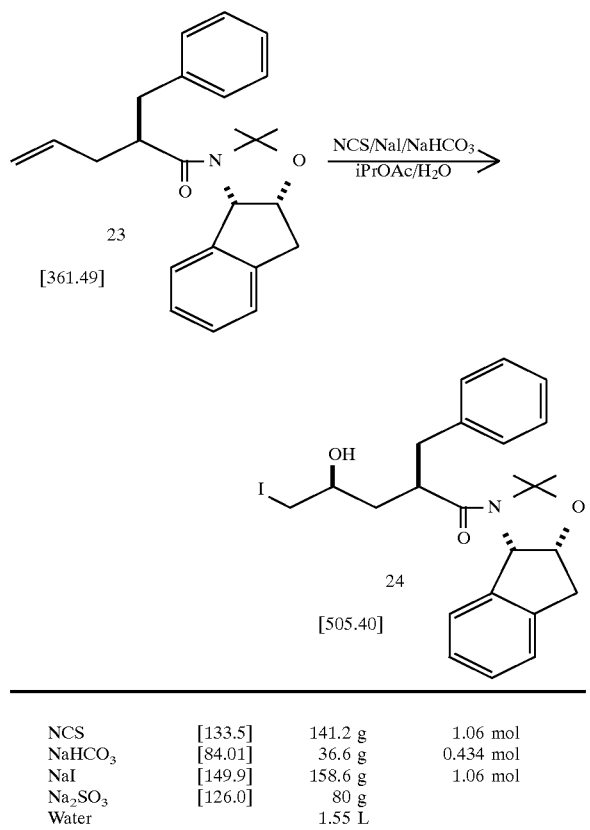

| NCS | [133.5] | 141.2 g | 1.06 mol |
| --- | --- | --- | --- |
| NaHCO₃ | [84.01] | 36.6 g | 0.434 mol |
| NaI | [149.9] | 158.6 g | 1.06 mol |
| Na₂SO₃ | [126.0] | 80 g | |
| Water | | 1.55 L | |

To the allyl amide 23 solution in IPAc from the previous step at 25° C. was added a solution of 36.6 g of sodium bicarbonate in 1.03 L of distilled water and the biphasic mixture was cooled to 5° C. Solid N-chlorosuccinimide (141.2 g, 1.06 mol) was added. There was no exotherm after the addition of NCS. To this mixture was added an aqueous solution of sodium iodide (158.6 g, 1.06 mol) while maintaining the reaction mixture at 6°–11° C. The addition took 30 min, and the mixture became dark. The mixture was warmed to 25° C. and aged with vigorous stirring. Progress of the reaction was monitored by HPLC: same system as above, approximate retention times: iodohydrins 24, epi-24, bis-epi-24=8.1 min; allyl amide 23=11.8 min. Analysis of the mixture by HPLC after 2.25 h indicated >99.5% conversion. The approximate diastereomer ratio of 24:epi-24:bis-epi-24 in the crude mixture is roughly 94:2:4 at this point when resolution of the components can be obtained on this system. The agitation was discontinued and the layers were separated. To the organic phase was added aqueous sodium sulfite (80 g, 0.635 mol in 400 mL) over 10–15 min. The temperature of the mixture rose from 26°–29° C. after the sodium sulfite addition. The mixture was agitated for 40 min at 25° C. The solution was substantially decolorized after the sulfite wash. The layers were separated; the KF of the organic phase at this point was 25 g/L. The volume of the organic phase was 1.97 L. Quantitative analysis of the mixture by HPLC (same system as above) indicated a 86% overall assay yield of the iodohydrin 24 at this point (corrected for coeluting diastereomers).

EXAMPLE 29

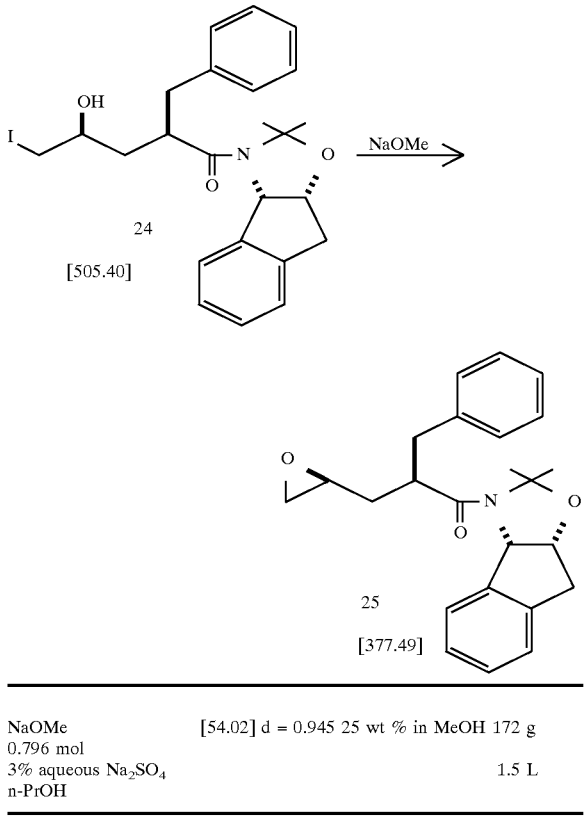

| NaOMe | [54.02] d = 0.945 25 wt % in MeOH 172 g |
| --- | --- |
| 0.796 mol | |
| 3% aqueous Na$_2$SO$_4$ | 1.5 L |
| n-PrOH | |

The solution of the iodohydrin 24 was concentrated in vacuo (28" Hg) to azeotropically dry the batch. A total of 700 mL of distillate was collected while maintaining a batch temperature of 22°–28° C. The distillate was replaced with 500 mL of IPAc (KF=275 mg/L).

The solution was cooled to 26° C. and 25% NaOMe/MeOH solution (168.1 g) was added over a 10 min period. The temperature dropped to 24° C. after the addition of sodium methoxide. The mixture became darker and a gummy solid briefly formed which redissolved. The mixture was aged for 1 h at 25° C. Analysis of the reaction was carried out by HPLC (same conditions as above), approximate retention times: epoxide epi-25=6.5 min, epoxide 25, bis-epi-25=7.1 min, iodohydrin 24=8.1 min. HPLC analysis indicated 99% conversion of the iodohydrin to the epoxide. After an additional 40 min, 4.1 g of the sodium methoxide/methanol solution was added. After 20 min, HPLC analysis indicated 99.5% conversion. The reaction was quenched by the addition of 366 mL of water at 25° C. which was then agitated briefly (10 min) and the layers were separated. It was subsequently found that extended aging of the reaction and water wash agitation/settling gave substantial back reaction to iodohydrin under these conditions in the pilot plant. This problem is especially acute in the water washes. To eliminate this problem, the reaction was run at 15° C. After >99% conversion was achieved (1 h after NaOMe addition), the mixture was diluted with IPAc (40% of batch volume) and initially washed with an increased volume of water (732 mL) at 20° C. Colder temperatures and more concentrated mixtures can result in the premature precipitation of 25 during the washes. The agitation/settling times were kept to a minimum (10 min/30 min, respectively). In this way, the back reaction could be limited to ≦1%. Crude mixtures containing (97:3) epoxide 25/iodohydrin 24 have been carried forward in the isolation to afford epoxide product containing 0.6% iodohydrin. Epoxide product containing this level of iodohydrin has been carried forward without complication. The organic phase was washed with 3% aqueous sodium sulfate (2×750 mL). The volume of the organic phase was 1.98 L after the washes. The pH of the three water washes was 10.7, 9.4 and 8.6, respectively. HPLC analysis indicated a 86% overall assay yield of epoxide 25 at this point (corrected for 4% co-eluting bis-epi-25). The IPAc solution of epoxide 25 was concentrated at reduced pressure (28" Hg) to a volume of about 600 mL while maintaining the batch at 15°–22° C. The solvent was switched to n-PrOH by adding 750 mL n-PrOH while vacuum concentrating to a pot volume of about 500 mL, maintaining the batch at <30° C. Temperatures >35° C. during the concentration/solvent switch can give an n-propyl ether as a degradation by-product derived from epoxide 25. Analysis of the solvent composition by $^1$H NMR showed <1 mol % EPAc remaining. The thick slurry was cooled to −10° C. over an hour and aged for 45 min. The solids were filtered and washed with 125 mL of cold nPrOH. The product was dried in a vacuum oven at 25° C. to afford 188.5 g of epoxide 25 (98.9 A %, 97.6 wt. %, 0.8 wt. % epi-25, 79.3% yield overall from 22.) Normal phase HPLC (see analytical research memo for procedure) indicated no bis-epi-25 present in the isolated solids.

EXAMPLE 30

Preparation of Penultimate 27

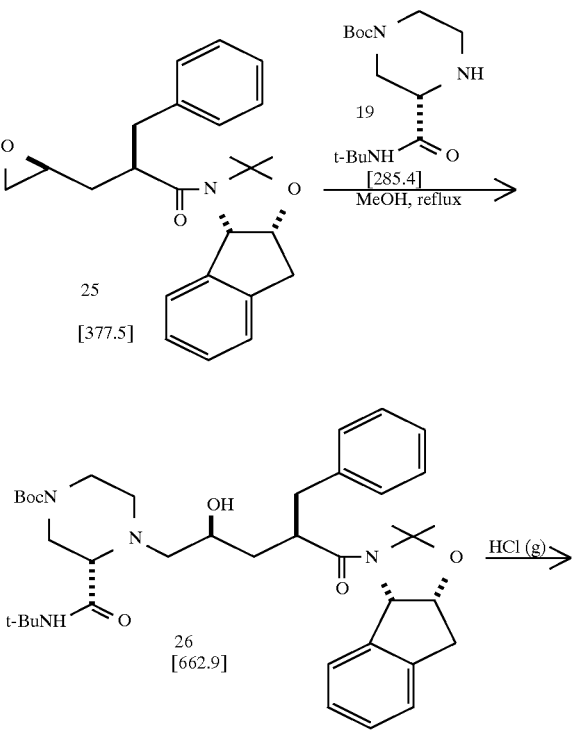

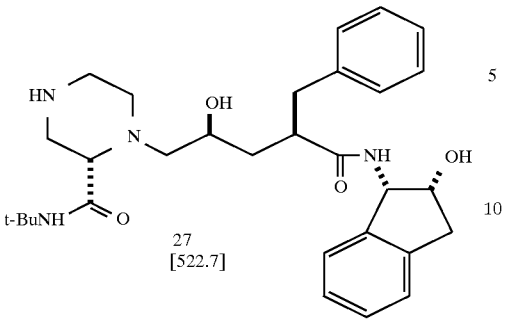

27
[522.7]

| | | |
|---|---|---|
| 2(S)-t-butylcarboxamide-4-N-Boc-piperazine 19 (98.9 wt. %, 99.6% ee) | 159 g | 557 mmol |
| epoxide 25 (97.6 wt. %, 1.0% epi-25) | 200 g | 530 mmol |
| methanol | 1.06 L | |
| HCl (g) | 194 g | 5.32 mol |
| 23% NaOH | 740 mL | |
| isopropyl acetate | 4.0 L | |
| water | 700 mL | |

*corrected for wt. % purity

Solid 2(S)-t-butylcarboxamide-4-t-butoxycarbonylpiperazine 3 (159 g, 557 mmol) and the epoxide 25 (200 g, 530 mol) were added to a 2 L three neck flask, equipped with a mechanical stirrer, reflux condenser, heating mantle, teflon coated thermocouple and nitrogen inlet. Methanol (756 mL) was added and the resulting slurry was heated to reflux temperature. After 40 min, a homogeneous solution was obtained. The internal temperature during reflux was 64°–65° C. Progress of the reaction was monitored by HPLC analysis: 60:40 acetonitrile/10 mM (KH$_2$PO$_4$/K$_2$HPO$_4$). Approximate retention times:

| retention time (min) | identity |
|---|---|
| 4.8 | piperazine 19 |
| 6.6 | methyl ether 28 |
| 8.2 | epoxide epi-25 |
| 8.9 | epoxide 25 |
| 15.2 | coupled product 26 |

The mixture was maintained at reflux until epoxide 25 was between 1.2 to 1.5 area % by HPLC analysis. The coupled product at this point was about 94–95 area %. The methyl ether 28 was present at 1.0–1.5 A % at completion. Typical time to achieve this conversion was 24–26 h at reflux.

epi-25

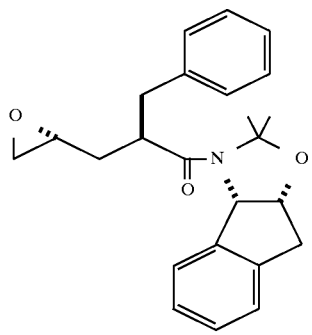

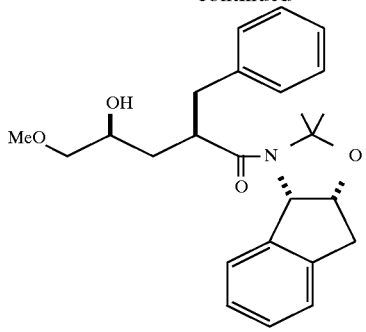

28

The mixture was cooled to −5° C. and anhydrous HCl gas (194 g, 5.32 moles, ~10 equiv.) was bubbled directly into the methanol solution under nitrogen atmosphere while keeping the temperature between 5°–8° C. over 2–3 h. After the addition was complete, the mixture was aged between 5°–8° C. for 1–3 h. Evolution of gas was observed at this point (carbon dioxide and isobutylene). Progress of the reaction was monitored by HPLC analysis: same conditions as above. Approximate retention times:

| retention time (min) | identity |
|---|---|
| 6.0 | Boc intermediate 29 |
| 7.0 | cis-aminoindanol 30 |
| 11.9 | penultimate 27 |
| 15.1 | coupled product 26 |
| 16.5 | lactone 31 |
| 25.0 | acetonide intermediate 32 |

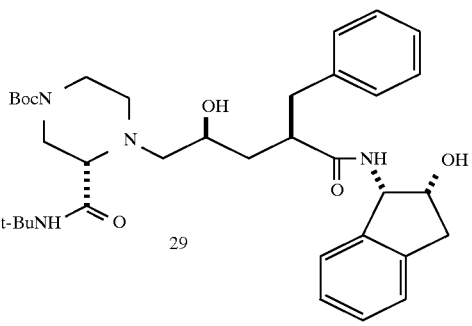

29

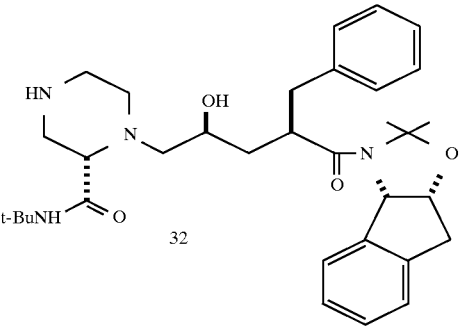

32

The mixture was aged at 5° to 8° C. until Boc intermediate 29 is <0.5 area % by HPLC analysis. At this point, penultimate 27 was about 92–93 A %, 30 was <1.0 A % and 31 was 0.6 A % by HPLC analysis. The deblocking was complete after 4 h at 5° C. Cooling and quenching the reaction promptly upon completion limits decompostion of 27 to 30 and 31 under the hydrolysis conditions.

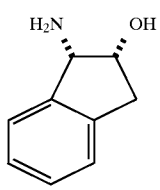
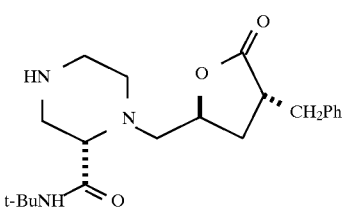

30    31

The mixture was cooled to −10° to −15° C. This mixture was then slowly added to a 5 liter flask equipped with a mechanical stirrer containing a cold, stirred solution of DI water (700 mL) and methanol (300 mL) at 0°–2° C.; the pH of the quenched mixture was maintained between 8.5–9.0 by addition of 23 wgt. % aqueous NaOH solution (giving a highly exothermic reaction) while keeping the temperature between 10°–20° C. The final batch pH was 9.0–9.5.

The mixture was extracted with isopropyl acetate (3.0 L). The mixture was agitated and the layers were separated. The spent aqueous phase was re-extracted with isopropyl acetate (1.0 L). HPLC assay yield of 27 in isopropyl acetate at this point is 94%.

The combined organic phase (~5.0 L) was concentrated under reduced pressure (24–25" of Hg) to a volume of about 1.12 L at a batch temperature of 30°–40° C. The pot temperature during the solvent switch can rise to 40° C. with no penalty in yield or degradation. This solution of crude 27 was then used directly in the next step to afford compound J.

EXAMPLE 31

Preparation of monohydrate

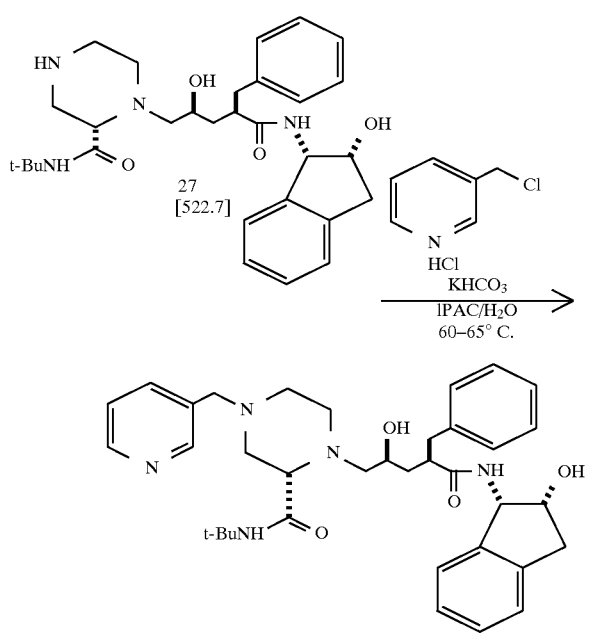

| penultimate 27 | 261 g | 499 mmol |
| potassium bicarbonate | 152 g | 1.52 mol |
| water | 6.1 L | |

-continued

| picolyl chloride | 93.3 g | 569 mmol |
| isopropyl acetate | 3.17 L | |

An isopropyl acetate solution of penultimate (4.96 L; 52.5 g/L of penultimate) was concentrated under reduced pressure to a volume of 1.18 L (260 g, 499 mmol). The batch temperature was maintained between 35° C. to 44° C. while keeping vacuum pressure at 25" of Hg. The methanol content was less than <1.0 vol %.

The resulting slurry was treated with an aqueous solution of potassium bicarbonate (152 g in 630 mL of water, 1.59 mol, ~3.0 equiv.) and heated to 60° C. Then, an aqueous solution of picolyl choride (93.8 g in 94 mL of water; 572 mmol, 1.14 equiv.) was added over 4 hours. The batch was seeded with compound J monohydrate after charging 75% of the picolyl chloride charge. The batch temperature was between 60° C. to 65° C.

At the end of the addition, the slurry mixture was aged for 20 h between 60° C. to 65° C. The reaction was complete when the penultimate is <1.0 area % by HPLC analysis. The picolyl chloride level was between 0.5 to 0.8 area %.

The batch was then diluted with 2.5 L of isopropyl acetate and 1.34 L of water and heated to 78° C. The layers were separated and the organic phase was washed with hot water (3×1.34 L) at 78° C. The hot water wash removed the bis-alkylated compound J and the level was reduced to <0.1 area % by HPLC analysis.

The organic phase was slowly cooled to 75° C. and seeded with compound J monohydrate (8.0 g) and then further cooled to 4° C. over 2 h. The mixture was filtered to collect the product and the wet cake was washed with cold isopropyl acetate (2×335 mL). The wet cake was dried in vacuo (28" Hg, 22° C.) to afford 273 g of compound J monohydrate in 79% isolated yield from the epoxide.

EXAMPLE 32

Pyrazine-2-tert-butyl carboxamide 34

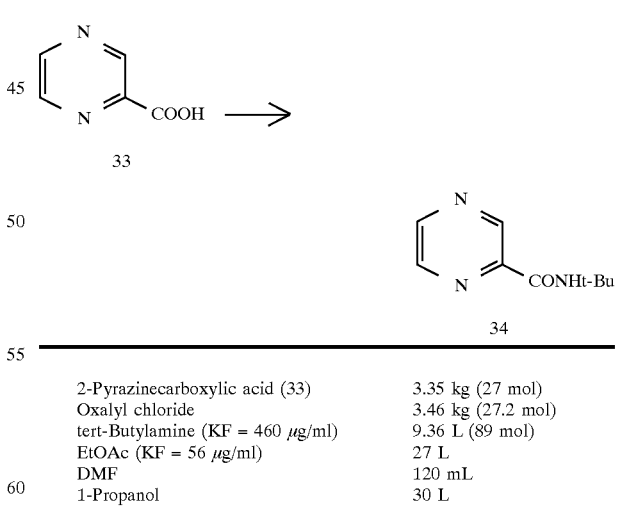

| 2-Pyrazinecarboxylic acid (33) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 33 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 33 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 33=10.7 min, amide 34=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 34 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atatmospheric pressure for several days.

Evaporation of an aliquot gave a tan solid m.p 87°–88° C. $^{13}C$ NMR (75 MHz, $CDCl_3$, ppm) 161.8, 146.8, 145.0, 143.8, 142.1, 51.0, 28.5.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A compound of the formula

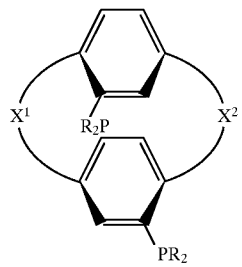

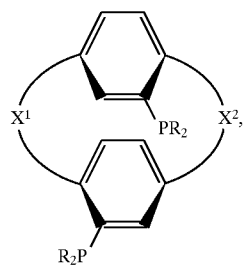

wherein R is $C_{1-4}$ alkyl, $C_{3-6}$ cycloalkyl, or aryl unsubstituted or substituted with —F, —$CH_3$, —$CF_3$ or $CH_3O$—; and $X^1$ and $X^2$ link the two $R_2P$-substituted benzenes and independently form a 2 to 4 membered link consisting of 2 to 4 carbon atoms.

2. The compound of claim 1, wherein the number of atoms in the $X^1$ link is the same as the number of atoms in the $X^2$ link.

3. The compound of claim 2, of the formula

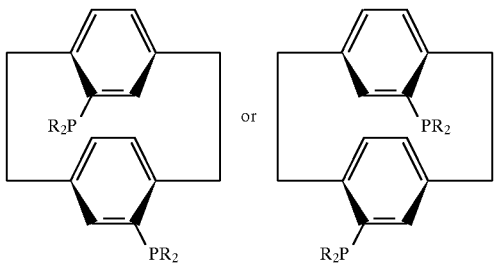

4. The compound of claim 3, of the formula

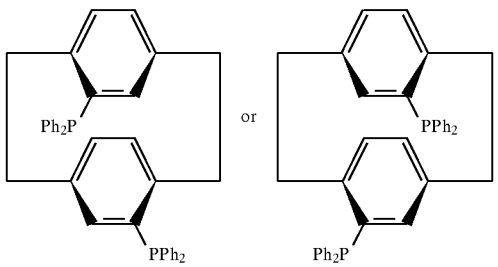

5. A process for forming a chiral bisphosphine compound (S)-40 or (R)-40

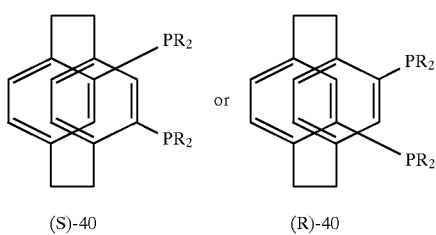

(S)-40          (R)-40 wherein R is $C_{1-4}$ alkyl, $C_{3-6}$ cycloalkyl, or aryl unsubstituted or substituted with —F, —CH$_3$, —CF$_3$ or CH$_3$O—; comprising the steps of (a) treating a racemic phosphinyl compound 41

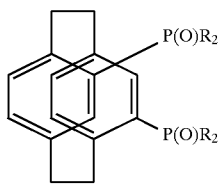   rac-41 with a resolving agent to afford chiral (S)-41 or (R)-41; and (b) reducing the chiral (S)-41 or (R)-41 to provide the chiral bisphosphine compound (S)-40 or (R)-40

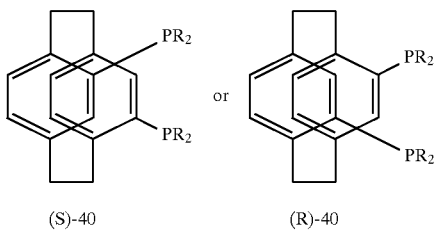

(S)-40          (R)-40

6. The process of claim 5, wherein the resolving agent is dibenzoyl-L-tartaric acid and each R is phenyl.

* * * * *